United States Patent
Kessman et al.

(10) Patent No.: US 6,968,224 B2
(45) Date of Patent: *Nov. 22, 2005

(54) METHOD OF DETECTING ORGAN MATTER SHIFT IN A PATIENT

(75) Inventors: Paul Kessman, Broomfield, CO (US); Troy Holsing, Louisville, CO (US); Jason Trobaugh, Louisville, CO (US)

(73) Assignee: Surgical Navigation Technologies, Inc., Louisville, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 10/664,646

(22) Filed: Sep. 19, 2003

(65) Prior Publication Data

US 2004/0059217 A1 Mar. 25, 2004

Related U.S. Application Data

(62) Division of application No. 10/047,927, filed on Jan. 14, 2002, now Pat. No. 6,669,635, which is a continuation of application No. 09/428,720, filed on Oct. 28, 1999, now Pat. No. 6,379,302.

(51) Int. Cl.$^7$ ............................................. A61B 5/05
(52) U.S. Cl. ..................... 600/407; 600/437; 128/916
(58) Field of Search ......................... 600/407–472; 367/7, 11, 130; 128/916; 345/419, 428, 582

(56) References Cited

U.S. PATENT DOCUMENTS

| | | |
|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,294,083 A | 12/1966 | Alderson |

(Continued)

FOREIGN PATENT DOCUMENTS

| | | |
|---|---|---|
| CA | 964149 | 3/1975 |
| DE | 3042343 A1 | 6/1982 |
| DE | 3831278 A1 | 3/1989 |
| DE | 4233978 C1 | 4/1994 |
| DE | 10085137 | 11/2002 |

(Continued)

OTHER PUBLICATIONS

"Prestige Cervical Disc System Surgical Technique", 12 pgs.

(Continued)

*Primary Examiner*—Ali Imam
(74) *Attorney, Agent, or Firm*—Harness, Dickey & Pierce, P.L.C.

(57) ABSTRACT

A surgical instrument navigation system comprises an ultrasound machine and a computer coupled to the ultrasound machine. A memory is coupled to the computer and includes computer instructions that when executed by the computer cause the computer to generate an icon representing the surgical instrument with a tip and the surgical instrument's trajectory and to overlay the icon on a real-time ultrasound image having an image plane, such that when the surgical instrument crosses the ultrasound image plane the format of the surgical instrument's trajectory is changed to represent the surgical instrument's crossing of the ultrasound image's plane. The system also comprises a localizer coupled to the ultrasound machine, and a display coupled to the computer for displaying the generated icon superimposed on the real-time image.

51 Claims, 13 Drawing Sheets

U.S. PATENT DOCUMENTS

| | | |
|---|---|---|
| 3,367,326 A | 2/1968 | Frazier |
| 3,439,256 A | 4/1969 | Kähne et al. |
| 3,577,160 A | 5/1971 | White |
| 3,674,014 A | 7/1972 | Tillander |
| 3,702,935 A | 11/1972 | Carey et al. |
| 3,704,707 A | 12/1972 | Halloran |
| 3,868,565 A | 2/1975 | Kuipers |
| 3,941,127 A | 3/1976 | Froning |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,202,349 A | 5/1980 | Jones |
| 4,262,306 A | 4/1981 | Renner |
| 4,287,809 A | 9/1981 | Egli et al. |
| 4,314,251 A | 2/1982 | Raab |
| 4,317,078 A | 2/1982 | Weed et al. |
| 4,328,813 A | 5/1982 | Ray |
| 4,339,953 A | 7/1982 | Iwasaki |
| 4,358,856 A | 11/1982 | Stivender et al. |
| 4,368,536 A | 1/1983 | Pfeiler |
| 4,396,885 A | 8/1983 | Constant |
| 4,403,321 A | 9/1983 | Kruger |
| 4,418,422 A | 11/1983 | Richter et al. |
| 4,422,041 A | 12/1983 | Lienau |
| 4,431,005 A | 2/1984 | McCormick |
| 4,485,815 A | 12/1984 | Amplatz et al. |
| 4,543,959 A | 10/1985 | Sepponen |
| 4,548,208 A | 10/1985 | Niemi |
| 4,572,198 A | 2/1986 | Codrington |
| 4,584,577 A | 4/1986 | Temple |
| 4,613,866 A | 9/1986 | Blood |
| 4,618,978 A | 10/1986 | Cosman |
| 4,621,628 A | 11/1986 | Bludermann |
| 4,625,718 A | 12/1986 | Olerud et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,673,352 A | 6/1987 | Hansen |
| 4,706,665 A | 11/1987 | Gouda |
| 4,719,419 A | 1/1988 | Dawley |
| 4,722,056 A | 1/1988 | Roberts et al. |
| 4,722,336 A | 2/1988 | Kim et al. |
| 4,727,565 A | 2/1988 | Ericson |
| 4,737,794 A | 4/1988 | Jones |
| 4,737,921 A | 4/1988 | Goldwasser et al. |
| 4,750,487 A | 6/1988 | Zanetti |
| 4,771,787 A | 9/1988 | Wurster et al. |
| 4,791,934 A | 12/1988 | Brunnett |
| 4,793,355 A | 12/1988 | Crum et al. |
| 4,797,907 A | 1/1989 | Anderton |
| 4,803,976 A | 2/1989 | Frigg et al. |
| 4,821,206 A | 4/1989 | Arora |
| 4,821,731 A | 4/1989 | Martinelli et al. |
| 4,836,778 A | 6/1989 | Baumrind et al. |
| 4,845,771 A | 7/1989 | Wislocki et al. |
| 4,849,692 A | 7/1989 | Blood |
| 4,862,893 A | 9/1989 | Martinelli |
| 4,889,526 A | 12/1989 | Rauscher et al. |
| 4,896,673 A | 1/1990 | Mathur et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,037,374 A | 8/1991 | Carol |
| 5,042,486 A | 8/1991 | Pfeiler et al. |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,150,715 A | 9/1992 | Ishiguro et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlöndorff et al. |
| 5,187,475 A | 2/1993 | Wagener et al. |
| 5,188,126 A | 2/1993 | Fabian et al. |
| 5,190,059 A | 3/1993 | Fabian et al. |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,628 A | 11/1993 | Ishiguro et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |

| Patent | Date | Inventor |
|---|---|---|
| 5,291,199 A | 3/1994 | Overman et al. |
| 5,295,483 A | 3/1994 | Nowacki et al. |
| 5,297,549 A | 3/1994 | Beatty et al. |
| 5,299,254 A | 3/1994 | Dancer et al. |
| 5,299,288 A | 3/1994 | Glassman et al. |
| 5,305,091 A | 4/1994 | Gelbart et al. |
| 5,305,203 A | 4/1994 | Raab |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,333,168 A | 7/1994 | Fernandes et al. |
| 5,345,938 A | 9/1994 | Nishiki et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Müller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,458,718 A | 10/1995 | Venkitachalam |
| 5,464,446 A | 11/1995 | Dreessen et al. |
| 5,478,341 A | 12/1995 | Cook et al. |
| 5,478,343 A | 12/1995 | Ritter |
| 5,480,422 A | 1/1996 | Ben-Haim |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlöndorff et al. |
| 5,503,320 A | 4/1996 | Webster et al. |
| 5,503,416 A | 4/1996 | Aoki et al. |
| 5,513,637 A | 5/1996 | Twiss et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,568,809 A | 10/1996 | Ben-haim |
| 5,572,999 A | 11/1996 | Funda et al. |
| 5,573,533 A | 11/1996 | Strul |
| 5,575,794 A | 11/1996 | Walus et al. |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,608,849 A | 3/1997 | King, Jr. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,268 A | 7/1997 | Vilsmeier et al. |
| 5,645,065 A | 7/1997 | Shapiro et al. |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,697,377 A | 12/1997 | Wittkampf |
| 5,702,406 A | 12/1997 | Vilsmeier et al. |
| 5,711,299 A | 1/1998 | Manwaring et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |

| | | |
|---|---|---|
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,765,561 A | 6/1998 | Chen et al. |
| 5,767,669 A | 6/1998 | Hansen et al. |
| 5,769,789 A | 6/1998 | Wang et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,866 A | 8/1998 | Sugiyama et al. |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,728 A | 9/1998 | Kuhn |
| 5,810,735 A | 9/1998 | Halperin et al. |
| 5,823,192 A | 10/1998 | Kalend et al. |
| 5,823,958 A | 10/1998 | Truppe |
| 5,828,725 A | 10/1998 | Levinson |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,884,410 A | 3/1999 | Prinz |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,938,603 A | 8/1999 | Ponzi |
| 5,938,694 A | 8/1999 | Jaraczewski et al. |
| 5,947,981 A | 9/1999 | Cosman |
| 5,950,629 A | 9/1999 | Taylor et al. |
| 5,951,475 A | 9/1999 | Gueziec et al. |
| 5,954,647 A | 9/1999 | Bova et al. |
| 5,964,796 A | 10/1999 | Imran |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,006,126 A | 12/1999 | Cosman |
| 6,016,439 A | 1/2000 | Acker |
| 6,019,725 A | 2/2000 | Vesely et al. |
| 6,021,342 A | 2/2000 | Brabrand |
| 6,024,695 A | 2/2000 | Taylor et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,073,043 A | 6/2000 | Schneider |
| 6,104,944 A | 8/2000 | Martinelli |
| 6,118,845 A | 9/2000 | Simon et al. |
| 6,122,538 A | 9/2000 | Sliwa, Jr. et al. |
| 6,131,396 A | 10/2000 | Duerr et al. |
| 6,139,183 A | 10/2000 | Graumann |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |
| 6,216,029 B1 | 4/2001 | Paltieli |
| 6,223,067 B1 | 4/2001 | Vilsmeier et al. |
| 6,233,476 B1 | 5/2001 | Strommer et al. |
| 6,246,231 B1 | 6/2001 | Ashe |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,332,089 B1 | 12/2001 | Acker et al. |
| 6,341,231 B1 | 1/2002 | Ferre et al. |
| 6,351,659 B1 | 2/2002 | Vilsmeier |
| 6,379,302 B1 * | 4/2002 | Kessman et al. ............ 600/437 |
| 6,381,485 B1 | 4/2002 | Hunter et al. |
| 6,424,856 B1 | 7/2002 | Vilsmeier et al. |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,470,207 B1 | 10/2002 | Simon et al. |
| 6,474,341 B1 | 11/2002 | Hunter et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,527,443 B1 | 3/2003 | Vilsmeier et al. |
| 6,551,325 B2 | 4/2003 | Neubauer et al. |
| 6,584,174 B2 | 6/2003 | Schubert et al. |
| 6,609,022 B2 | 8/2003 | Vilsmeier et al. |
| 6,611,700 B1 | 8/2003 | Vilsmeier et al. |
| 6,640,128 B2 | 10/2003 | Vilsmeier et al. |
| 6,694,162 B2 | 2/2004 | Hartlep |
| 6,701,179 B1 | 3/2004 | Martinelli et al. |

FOREIGN PATENT DOCUMENTS

| | | |
|---|---|---|
| EP | 0 319 844 A1 | 1/1988 |
| EP | 0419729 A1 | 9/1989 |
| EP | 0350996 A1 | 1/1990 |
| EP | 0 651 968 A1 | 8/1990 |
| EP | 0 581 704 B1 | 7/1993 |

| | | |
|---|---|---|
| EP | 0 655138 B1 | 4/1998 |
| EP | 0 894473 A2 | 2/1999 |
| EP | 0 922 438 A1 | 6/1999 |
| FR | 2417970 | 2/1979 |
| JP | 2765738 | 6/1998 |
| WO | WO 88/09151 | 12/1988 |
| WO | WO 89/05123 | 6/1989 |
| WO | WO 91/03982 | 4/1991 |
| WO | WO 91/04711 | 4/1991 |
| WO | WO 91/07726 | 5/1991 |
| WO | WO 92/03090 | 3/1992 |
| WO | WO 92/06645 | 4/1992 |
| WO | WO 94/04938 | 3/1994 |
| WO | WO 94/23647 | 10/1994 |
| WO | WO 94/24933 | 11/1994 |
| WO | WO 96/11624 | 4/1996 |
| WO | WO 96/25881 | 8/1996 |
| WO | WO 97/03609 | 2/1997 |
| WO | WO 98/08554 | 3/1998 |
| WO | WO 98/38908 | 9/1998 |
| WO | WO 99/60939 | 1/1999 |
| WO | WO 01/30437 A1 | 5/2001 |

OTHER PUBLICATIONS

Adams et al., "Orientation Aid for Head and Neck Surgeons," Innov. Tech. Biol. Med., vol. 13, No. 4, 1992, pp. 409–424.

Barrick et al., "Prophylactic Intramedullary Fixation of the Tibia for Stress Fracture in a Professional Athlete," Journal of Orthopaedic Trauma, vol. 6, No. 2, pp. 241–244 (1992).

Barrick et al., "Technical Difficulties with the Brooker–Wills Nail in Acute Fractures of the Femur," Journal of Orthopaedic Trauma, vol. 6, No. 2, pp. 144–150 (1990).

Barrick, "Distal Locking Screw Insertion Using a Cannulated Drill Bit: Technical Note," Journal of Orthopaedic Trauma, vol. 7, No. 3, 1993, pp. 248–251.

Batnitzky et al., "Three–Dimensional Computer Reconstructions of Brain Lesions from Surface Contours Provided by Computed Tomography: A Prospectus," Neurosurgery, vol. 11, No. 1, Part 1, 1982, pp. 73–84.

Bouazza–Marouf et al.; "Robotic–Assisted Internal Fixation of Femoral Fractures", IMECHE., pp. 51–58 (1995).

Brack et al., "Accurate X–ray Based Navigation in Computer–Assisted Orthopedic Surgery," CAR '98, pp. 716–722.

Bryan, "Bryan Cervical Disc System Single Level Surgical Technique", Spinal Dynamics, 2002, pp. 1–33.

Champleboux et al., "Accurate Calibration of Cameras and Range Imaging Sensors: the NPBS Method," IEEE International Conference on Robotics and Automation, Nice, France, May, 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254–263.

Cinquin et al., "Computer Assisted Medical Interventions," International Advanced Robotics Programme, Sep. 1989, pp. 63–65.

Feldmar et al., "3D–2D Projective Registration of Free–Form Curves and Surfaces," Rapport de recherche (Inria Sophia Antipolis), 1994, pp. 1–44.

Foley et al., "Fundamentals of Interactive Computer Graphics," The Systems Programming Series, Chapter 7, Jul. 1984, pp. 245–266.

Gildenberg et al., "Calculation of Stereotactic Coordinates from the Computed Tomographic Scan," Neurosurgery, vol. 10, No. 5, May 1982, pp. 580–586.

Gonzalez, "Digital Image Fundamentals," Digital Image Processing, Second Edition, 1987, pp. 52–54.

Gottesfeld Brown et al., "Registration of Planar Film Radiographs with Computer Tomography," Proceedings of MMBIA, Jun. '96, pp. 42–51.

Gueziec et al., "Registration of Computed Tomography Data to a Surgical Robot Using Fluoroscopy: A Feasibility Study," Computer Science/Mathematics, Sep. 27, 1996, 6 pages.

Hamadeh et al, "Kinematic Study of Lumbar Spine Using Functional Radiographies and 3D/2D Registration," TIMC UMR 5525—IMAG.

Hamadeh et al., "Automated 3–Dimensional Computed Tomographic and Fluorscopic Image Registration," Computer Aided Surgery (1998), 3:11–19.

Hamadeh et al., "Towards Automatic Registration Between CT and X–ray Images: Cooperation Between 3D/2D Registration and 2D Edge Detection," MRCAS '95, pp. 39–46.

Hoerenz, "The Operating Microscope I. Optical Principles, Illumination Systems, and Support Systems," Journal of Microsurgery, vol. 1, 1980, pp. 364–369.

Hofstetter et al., "Fluoroscopy Based Surgical Navigation—Concept and Clinical Applications," Computer Assisted Radiology and Surgery, 1997, pp. 956–960.

Horner et al., "A Comparison of CT–Stereotaxic Brain Biopsy Techniques," Investigative Radiology, Sep.–Oct. 1984, pp. 367–373.

Hounsfield, "Computerized transverse axial scanning (tomography): Part 1. Description of system," British Journal of Radiology, vol. 46, No. 552, Dec. 1973, pp. 1016–1022.

Jacques et al., "A Computerized Microstereotactic Method to Approach, 3–Dimensionally Reconstruct, Remove and Adjuvantly Treat Small CNS Lesions," Applied Neurophysiology, vol. 43, 1980, pp. 176–182.

Jacques et al., "Computerized three–dimensional stereotaxic removal of small central nervous system lesion in patients," J. Neurosurg., vol. 53, Dec. 1980, pp. 816–820.

Joskowicz et al., "Computer–Aided Image–Guided Bone Fracture Surgery: Concept and Implementation," CAR '98, pp. 710–715.

Kelly et al., "Computer–assisted stereotaxic laser resection of intra–axial brain neoplasms," Journal of Neurosurgery, vol. 64, Mar. 1986, pp. 427–439.

Kelly et al., "Precision Resection of Intra–Axial CNS Lesions by CT–Based Stereotactic Craniotomy and Computer Monitored CO2 Laser," Acta Neurochirurgica, vol. 68, 1983, pp. 1–9.

Laitinen et al., "An Adapter for Computed Tomography–Guided, Stereotaxis," Surg. Neurol., 1985, pp. 559–566.

Laitinen, "Noninvasive multipurpose stereoadapter," Neurological Research, Jun. 1987, pp. 137–141.

Lavallee et al., "Computer Assisted Interventionist Imaging: The Instance of Stereotactic Brain Surgery," North–Holland MEDINFO 89, Part 1, 1989, pp. 613–617.

Lavallee, "VI Adaption de la Methodologie a Quelques Applications Cliniques," Chapitre VI, pp. 133–148.

Leksell et al., "Stereotaxis and Tomography—A Technical Note," ACTA Neurochirurgica, vol. 52, 1980, pp. 1–7.

Lemieux et al., "A Patient–to–Computed–Tomography Image Registration Method Based on Digitally Reconstructed Radiographs," Med. Phys. 21 (11), Nov. 1994, pp. 1749–1760.

Mazier et al., "Computer–Assisted Interventionist Imaging: Application to the Vertebral Column Surgery," Annual International Conference of the IEEE Engineering in Medicine and Biology Society, vol. 12, No. 1, 1990, pp. 0430–0431.

Mazier et al., Chirurgie de la Colonne Vertebrate Assistee par Ordinateur: Appication au Vissage Pediculaire, Innov. Tech. Biol. Med., vol. 11, No. 5, 1990, pp. 559–566.

Phillips et al., "Image Guided Orthopaedic Surgery Design and Analysis," Trans Inst. MC, vol. 17, No. 5, 1995, pp. 251–264.

Potamianos et al., "Intra–Operative Imaging Guidance for Keyhole Surgery Methodology and Calibration," First International Symposium on Medical Robotics and Computer Assisted Surgery, Sep. 22–24, 1994, pp. 98–104.

Reinhardt et al., "CT–Guided 'Real–Time' Stereotaxy," ACTA Neurochirurgica, 1989.

Roberts et al., "A frameless stereotaxic integration of computerized tomographic imaging and the operating microscope," J. Neurosurg., vol. 65, Oct. 1986, pp. 545–549.

Rosenbaum et al., "Computerized Tomography Guided Stereotaxis: A New Approach," Applied Neurophysiology, vol. 43, No. 3–5, 1980, pp. 172–173.

Sautot, "Vissage Pediculaire Assiste Par Ordinateur," Sep. 20, 1994.

Schueler et al., "Correction of Image Intensifier Distortion for Three–Dimensional X–Ray Angiography," SPIE Medical Imaging 1995, vol. 2432, pp. 272–279.

Selvik et al., "A Roentgen Stereophotogrammetric System," Acta Radiologica Diagnosis, 1983, pp. 343–352.

Shelden et al., "Development of a computerized microstereotaxic method for localization and removal of minute CNS lesions under direct 3–D vision," J. Neurosurg., vol. 52, 1980, pp. 21–27.

The Laitinen Stereotactic System, E2–E6.

Viant et al., "A Computer Assisted Orthopaedic System for Distal Locking of Intramedullary Nails," Proc. of MediMEC '95, Bristol, 1995, pp. 86–91.

Watanabe et al., "Three–Dimensional Digitizer (Neuronavigator): New Equipment for Computed Tomography–Guided Stereotaxic Surgery," Surgical Neurology, vol. 27, No. 6, Jun. 1987, pp. 543–547.

Watanabe, "Neuronavigator," Igaku–no–Ayumi, vol. 137, No. 6, May 10, 1986, pp. 1–4.

Weese et al., "An Approach to 2D/3D Registration of a Vertebra in 2D X–ray Fluoroscopies with 3D CT Images," pp. 119–128.

Germano, "Instrumentation, Technique and Technology", Neurosurgery, vol. 37, No. 2, Aug., 1995, pp. 348–350.

Merloz, et al., "Computer Assisted Spine Surgery", Clinical Assisted Spine Surgery, No. 337, pp. 86–96.

Hatch, et al., "Reference–Display System for the Integration of CT Scanning and the Operating Microscope", Proceedings of the Eleventh Annual Northeast Bioengineering Conference, Mar. 14–15, 1985, pp. 252–254.

International Search Report, Apr. 20, 2001.

C. Davatzikos, et al., "Brain Image Registration Based on Curve Mapping," IEEE, 0–8186–5802–Sep. 1994 pp. 245–254.

Stereotactic Image Systems, Inc., "Affordable PC Based Graphics for Stereotactic Surgery," Stereotactic One, Scantec, Inc. undated.

K. Foley, "The StealthStation™: Three–Dimensional Image–Interactive Guidance for the Spine Surgeon," Spine Frontiers (Apr. 1996) pp. 7–9.

S. Lavallée, et al., Matching 3–D Smooth Surfaces with their 2–D Projections using 3–D Distance Maps, SPIE, Geometric Methods in Computer Vision, vol. 1570, (Jul. 25–26, 1991) pp. 322–336.

Sulzer Orthopedics Ltd., Product Information, "NAVITRACK™ Computer Assisted Surgery System," SULZERMEDICA, Edition 3/98.

K. Foley, "Image Guided Spine Surgery Utilizing Frameless Stereotaxy," presentation papers (undated).

Product Information on The Laitinen Stereotactic System, . . . opening new doors in stereotaxis, (undated).

D. Norman, et al., "Localization with the EMI Scanner," The American Journal of Roentgenology Radium Therapy and Nuclear Medicine, vol. 125, No. 4, (Dec. 1975) pp. 961–964.

R. Levinthal, "Technique for Accurate Localization with the CT Scanner," Bulletin of the Los Angeles Neurological Societies, vol. 41, No. 1, (Jan. 1976) pp. 6–8.

M. Bergström, et al., "Stereotaxic Computed Tomography," The American Journal of Roentgenology, vol. 127 (1976) pp. 167–170.

R. Penn, et al., "Stereotactic Surgery with Image Processing of Computerized Tomographic Scans," Neurosurgery, vol. 3, No. 2 (1978) pp. 157–163.

F. Mundinger, "Treatment of Small Cerebral Gliomas with CT–Aided Stereotaxic Curietherapy," Neuroradiology, vol. 16, (Dec. 15, 1978) pp. 564–567.

D. O'Leary, "Localization of vertex lesions seen on CT scan," Journal of Neurosurgery, vol. 49, Jul. 1978), pp. 71–74.

R. Brown, "A computerized tomography–computer graphics approach to stereotaxic localization," Journal of Neurosurgery, vol. 50, No. 6, (Jun. 1979), pp. 715–720.

J. Boëthius, "Stereotaxic computerized tomography with a GE 8800 scanner," Journal of Neurosurgery, vol. 52, No. 6, (Jun. 1980) pp. 794–800.

M. Heilbrun, "Computed Tomography–Guided Stereotactic Systems," Computed Tomographic Stereotaxy, Chapter 31 (undated) pp. 564–581.

G. Selvik, et al., "A Roentgen Stereophotogrammetric System," Acta Radiologica Diagnosis, vol. 24, No. 4 (1983) pp. 343–352.

M. Heilbrun, et al., "Preliminary experience with Brown–Roberts–Wells (BRW) computerized tomography stereotaxic guidance system," Journal of Neurosurgery, vol. 59, Aug. 9, 1983), pp. 217–222.

A. Patil, "Computed Tomography Plane of the Target Approach in Computed Tomographic Stereotaxis," Neurosurgery, vol. 15, No. 3, (Sep. 1984) pp. 410–414.

J. Hatch, "Reference–Display System for the Integration of CT Scanning and the Operating Microscope," Thesis, Thayer School of Engineering, Dartmouth College, (1984) 189 pages.

Y. Kwoh, "A Robot with Improved Absolute Positioning Accuracy for CT Guided Stereotactic Brain Surgery," IEEE Transactions on Biomedical Engineering, vol. 35, No. 2, (Feb. 1988) pp. 153–160.

Y. Kosugi, et al., "An Articulated Neurosurgical Navigation System Using MRI and CT Images," IEEE Transactions of Biomedical Engineering, vol. 35, No. 2, (Feb. 1988) pp. 147–152.

E. Friets, "A Frameless Stereotaxic Operating Microscope for Neurosurgery," IEEE Transactions on Biomedical Engineering, vol. 36, No. 6, (Jun. 1999) pp. 608–617.

S. Lavallee, "A New System for Computer Assisted Neurosurgery," IEEE Engineering in Medicine and Biology Society 11$^{th}$ Annual International Conference, (1989) 2 pages.

S. Lavallee, edited by H. Lemke et al., "Computer Assisted Driving of a Needle into the Brain," Computer Assisted Radiology (1989) pp. 416–420.

D. Levin, et al, "Multimodality 3–D views of the Brain Created from MRI and PET scans," Magnetic Resonance Imaging, Special Issue: SMRI Seventh Annual Meeting Program and Abstracts, vol. 7, Supplement 1 (1989) p. 89.

C. Pelizzari, "Accurate Three–Dimensional Registration of CT, PET, and/or MR Images of the Brain," Journal of Computer Assisted Tomography, vol. 13, No. 1 (Jan./Feb. 1989) pp. 20–26.

D. Levin, "The Brain: Integrated Three–dimensional Display of MR and PET Images," Radiology, vol. 172, No. 3, (Sep. 1989) p. 783–789.

S. Lavallee, et al., "Computer Assisted Medical Interventions," NATO ASI Series, vol. F, No. 60 (1990) pp. 301–312.

W. Krybus, et al., "Navigation Support for Surgery by Means of Optical Position Detection," Proceedings of the International Symposium. CAR '91 Computer Assisted Radiology, pp. 362–366.

P. Kelly, "Stereotactic Imaging, Surgical Planning and Computer–Assisted Resection of Intracranial Lesions: Methods and Results," Advances and Technical Standards in Neurosurgery, vol. 17, (1990) pp. 77–118.

L. Adams, et al., "Computer–Assisted Surgery," Medical Imaging, IEEE Computer Graphics and applications, (May, 1990).

A. Kato, "A frameless, armless navigational system for computer–assisted neurosurgery," Journal of Neurosurgery, vol. 74, (May 1991) pp. 845–849.

S. Lavallee, et al., "Matching of Medical Images for Computed and Robot Assisted Surgery," TIMB–IMAG, Faculte de Medecine de Grenoble, undated, 2 pages.

Reported by Bill Dever, RT associate editor, "3–D in the OR, guided endoscopic surgery," Radiology Today (Feb. 1991) 2 pages.

L. Holman, "Computer–Assisted Superimposition of Magnetic Resonance and High–Resolution Technetium–99m–HMPAO and Thallium–201 SPECT Images of the Brain," The Journal of Nuclear Medicine, vol. 32, No. 8, (Aug. 1991) pp. 1478–1484.

K. Smith, "Multimodality Image Analysis and Display Methods for Improved Tumor Localization in Stereotactic Neurosurgery," Annual International Conference of the IEEE Engineering in Medicine and Biology Society, vol. 13, No. 1 (1991) p. 0210.

P. Clarysse, "A Computer–Assisted System for 3–D Frameless Localization in Stereotaxic MRI," IEEE Transactions in Medical Imaging, vol. 10, No. 4, (Dec. 1991) pp. 523–529.

L. Adams, et al., "Orientation Aid for Head and Neck Surgeons," Innov. Tech. Biol. Med., vol. 13, No. 4, (1992) pp. 410–424.

K. Smith, "Computer Methods for Improved Diagnostic Image Display Applied to Stereotactic Neurosurgery," Stereotactic Neurosurgery Display (Nov. 1991) pp. 371–386.

K. Obergfell, et al., "End–Point Position Measurements of Long–Reach Flexible Manipulators," Georgia Institute of Technology, School of Mechanical Engineering, (undated).

P. Cinquin, et al., IGOR: "Image Guided Operating Robot. Methodology, Applications," TIMB–IMAG, Faculte de Medecine de Grenoble (undated) pp. 1–2.

M. Heilbrun, et al., "Stereotactic Localization and Guidance Using a Machine Vision Technique," Stereotactic and Functional Neurosurgery, 58/1–4/92 (Sep. 1992) pp. 94–98.

L. Klimek, et al., "Long–Term Experience with Different Types of Localization Systems in Skull–Base Surgery," Ear, Nose and Throat Surgery, (undated) pp. 635–638.

R. Bucholz, et al., "Intraoperative localization using a three–dimensional optical digitizer," SPIE Proceedings of Clinical Applications of Modern Imaging Technology, vol. 1894 (Jan. 17–19, 1993) pp. 312–322.

R. Bucholz, et al., "Variables affecting the accuracy of stereotactic localization using computerized tomography," Journal of Neurosurgery, vol. 79, (Nov. 1993) pp. 667–673.

S. Lavallee, et al., "Computer Assisted Spine Surgery: a technique for accurate transpedicular screw fixation using CT data and a 3–D optical localizer," TIMC, Faculte de Medecine de Grenoble, (undated) pp. 315–322.

C. Gallen, et al., "Intracranial Neurosurgery Guided by Functional Imaging," Surg. Neurol., vol. 42, (1994) pp. 523–530.

J. Henderson, "An Accurate and Ergonomic Method of Registration for Image–Guided Neurosurgery," Computerized Medical Imaging and Graphics, vol. 18, No. 4, (Jul.–Aug. 1994) pp. 273–277.

K. Smith, "The Neurostation™–a Highly Accurate, Minimally Invasive Solution to Frameless Stereotactic Neurosurgery," Computerized Medical Imaging and Graphics, vol. 18, No. 4, (1994) pp. 247–256.

S. Lavallee, "Image guided operating robot: a clinical application in stereotactic neurosurgery," First International Symposium on Medical Robotics and Computer Assisted Surgery, IEEE vol. 92 (Sep. 22–24, 1994) pp. 618–624.

E. Benzel, "Magnetic Source Imaging: A Review of the Magnes System of Biomagnetic Technologies Incorporated," Neurosurgery, vol. 33, No. 2, Aug. 1993) pp. 252–259.

D. Kondiziolka, et al., "Guided Neurosurgery Using the ISG Viewing Wand," vol. 17, No. 8 (1995) pp. 1–6.

J. Golfinos, et al., "Clinical use of a frameless stereotactic arm: results of 325 cases," Journal of Neurosurgery, vol. 83 (Aug. 1995) pp. 197–205.

P. Kelly, "The NeuroStation System for Image–Guided, Frameless Stereotaxy," Neurosurgery, vol. 37, No. 2 (Aug. 1995) pp. 348–350.

K. Foley, et al., "Image–guided Intraoperative Spinal Localization," reprinted from Intraoperative Neuroprotection, Chapter 19, Part Three Intraoperative Neuroprotection: Monitoring (1996) pp. 325–340.

R. Bucholz, et al., "Image–guided Surgical Techniques for Infections and Trauma of the Central Nervous System," Clinical Frontiers of Interactive Image–Guided Neurosurgery, vol. 7, No. 2, (Apr. 1996), pp. 187–200.

C. Siegel, "Creating 3D Movies from Medical Images Using AVS," Hippocrates Project, N.Y.U. School of Medicine (undated), 4 pages.

R. Bucholz, "Intraoperative Ultrasonic Brain Shift Monitor and Analysis," St. Louis University Hospital (undated) 2 pages.

R. Bucholz, "The Correction of Stereotactic Inaccuracy Caused by Brain Shift Using an Intraoperative Ultrasound Device," VCRMed–MRCAS'97 (Mar. 19–22, 1997) pp. 459–466.

W. Grimson, et al., "Image–Guided Surgery," Scientific American (Jun. 1999) pp. 63–69.

C. Pelizzari, "Interactive 3D Patient–Image Registration," Computer Science 511, Information Processing in Medical Imaging (Jul. 1991) pp. 132–141.

C.A. Pelizzari, et al., "Three Dimensional Correlation of PET, CT and MRI Images," Abstract No. 528, The Journal of Nuclear Medicine, Abstract Book, Proceedings of the $34^{th}$ Annual Meeting, vol. 28, No. 4, (Apr. 1997) p. 682.

Product Information on Vector Vision, SooooOO Easy, BrainLAB GmbH (undated).

* cited by examiner

METHOD OF DETECTING ORGAN MATTER SHIFT IN A PATIENT

CROSS REFERENCE TO RELATED APPLICATIONS

This application is a divisional of U.S. Ser. No. 10/047,927, filed Jan. 14, 2002, now U.S. Pat. No. 6,669,635, issued Dec. 30, 2003, which is a continuation of U.S. Ser. No. 09/428,720, filed Oct. 28, 1999, now U.S. Pat. No. 6,379,302, issued Apr. 30, 2002. The disclosures of the above applications and/or patents are incorporated herein by reference.

CONCURRENTLY FILED APPLICATIONS

The following United States patent applications, which were concurrently filed with this one on Oct. 28, 1999, are fully incorporated herein by reference: Method and System for Navigating a Catheter Probe in the Presence of Field-influencing Objects, by Michael Martinelli, Paul Kessman and Brad Jascob; Patient-shielding and Coil System, by Michael Martinelli, Paul Kessman and Brad Jascob; Coil Structures and Methods for Generating Magnetic Fields, by Brad Jascob, Paul Kessman and Michael Martinelli; Registration of Human Anatomy Integrated for Electromagnetic Localization, by Mark W. Hunter and Paul Kessman; System for Translation of Electromagnetic and Optical Localization Systems, by Mark W. Hunter and Paul Kessman; Surgical Communication and Power System, by Mark W. Hunter, Paul Kessman and Brad Jascob; and Surgical Sensor, by Mark W. Hunter, Sheri McCoid and Paul Kessman.

1. Field of the Invention

The present invention is directed generally to image guided surgery, and more particularly, to systems and methods for surgical navigation using one or more real-time ultrasound images overlaid onto pre-acquired images from other image modalities.

2. Description of the Related Art

Physicians have used pre-acquired ultrasound images to plan surgery for many years. Traditionally, ultrasound machines provide two-dimensional images of the relevant human anatomy. Physicians use such images to diagnose, among other things, fetal deformities. However, until recently, physicians have not used such ultrasound images that have been either pre-acquired or acquired in real time during surgery for surgical navigation purposes.

Some recent systems permit the use of ultrasound images in conjunction with a specialized software running on a computer to plan and execute a surgery. For example, among other systems, the Ultraguide system permits a physician to represent an icon representation of a surgical instrument on an ultrasound image. This system also plots a trajectory of a surgical instrument's probe on a two-dimensional ultrasound image.

Similarly, the Life Imaging system also provides some help to a physician by converting two-dimensional ultrasound images into a three-dimensional cube. Subsequently, the physician may view an iconic representation of a surgical instrument on the cube.

However, none of these systems permit a physician to overlay images from other image modalities over ultrasound images along with a display of a surgical instrument on the overlaid images.

SUMMARY OF THE INVENTION

Objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

One aspect of the present invention is directed to a surgical navigation system comprising several devices. In particular, the surgical navigation system includes an ultrasound machine, a computer coupled to the ultrasound machine, such that image data corresponding to the images acquired by the ultrasound machine can be transferred to the computer. In addition, the surgical navigation system includes a memory coupled to the computer which has computer instructions. The computer instructions when executed by the computer cause the computer to generate an icon representing the surgical instrument with a tip and the surgical instrument's trajectory and to overlay the icon on a real-time ultrasound image, such that when the surgical instrument crosses the ultrasound image plane the format of the surgical instrument's trajectory is changed to represent the surgical instrument's crossing of the ultrasound image's plane. Furthermore, the surgical navigation system includes a localizer coupled to the ultrasound machine, which permits the system to localize the ultrasound probe, a part of the ultrasound machine. Finally, the surgical navigation system includes a display coupled to the computer for displaying the generated icon superimposed on the real-time ultrasound image acquired by the ultrasound machine.

The surgical navigation system further includes a display which can display a side view of the ultrasound image with a representation of the surgical instrument's trajectory displaying the angle at which the surgical instrument's trajectory intersects with the ultrasound image. In addition, the claimed system can calculate the angle at which the surgical instrument's trajectory intersects with the ultrasound image. Moreover, the claimed system can also represent the angle at which the surgical instrument's trajectory intersects with the ultrasound image using periodic markers.

Another surgical navigation system consistent with the present invention includes, an ultrasound machine and a video imaging device, such as a laparoscope where the ultrasound machine and the video-imaging device are coupled to the computer in a way that image data from both of these devices can be transferred to the computer. Alternatively, the video imaging device may also be an X-ray machine. In addition, the surgical navigation system has localizers attached to both the ultrasound machine and to the video imaging device. Furthermore, the system includes, a memory coupled to the computer, where the memory includes computer instructions. The computer instructions when executed by the computer cause the computer to overlay the video images acquired by the video imaging device onto the ultrasound image acquired by the ultrasound device such that the two images correspond to a common coordinate system. Finally, the system includes a display that can display the overlaid images.

In addition to the above mentioned systems, the concepts of the present invention may be practiced as a number of related methods.

One method consistent with the present invention is surgical navigation using images from other image modalities overlaid over ultrasound images. The method comprises calibrating the system, a step which need be performed initially only; registering image data-sets from other image modalities to patient anatomy, a physician scanning an area of interest using the ultrasound probe; the computer overlaying images from other image modalities onto the ultrasound images; the physician moving the ultrasound probe or other surgical instruments; and the system calculating a new location of the surgical instruments.

Another method consistent with the present invention is a method for calculating and displaying an ultrasound probe's angle relative to an ultrasound image plane. The method comprises drawing a circle with its center at the point where the ultrasound probe's trajectory crosses the ultrasound image plane. The circle's radius represents the angle of the ultrasound probe relative to the ultrasound image plane. The angle of the ultrasound probe relative to the ultrasound image plane may also be displayed using periodic markers consistent with the present invention.

Still another method consistent with the present invention is a method to overlay image segmentations onto ultrasound images for surgical navigation. The method comprises extracting a two dimensional image from the three-dimensional image data-set; overlaying the extracted segmentation onto an ultrasound image corresponding to the same human anatomy; displaying the overlaid image along with an iconic representation of the surgical instruments; the physician moving the ultrasound probe or other surgical instruments; and the system calculating a new location of the surgical instruments.

An additional method consistent with the present invention is surgical navigation using three-dimensional image data-sets. The method comprises a physician acquiring a three-dimensional ultrasound image data-set; a computer reconstructing the image data-set into an orthogonal data-set; displaying the three-dimensional image on a display along with an iconic representation of the surgical instruments; the physician moving the ultrasound probe or other surgical instruments; and the system calculating a new location of the surgical instruments.

Yet another method consistent with the present invention is a method for detecting organ-matter shift from the time when CT or MR image data-sets are created to the time when the patient is operated upon. The method comprises correlating a real-time ultrasound image and a pre-acquired three-dimensional image to obtain a correlated two-dimensional image; selecting a first set of points on the real-time ultrasound image; selecting a corresponding second set of points on the correlated two-dimensional image; and displaying a vector representing the distance and the direction of the organ-matter shift.

It is to be understood that both the foregoing general description and the following detailed description are exemplary and explanatory only and are not restrictive of the invention, as claimed.

The accompanying drawings, which are incorporated in and constitute a part of this specification, illustrate one (several) embodiment(s) of the invention and together with the description, serve to explain the principles of the invention.

BRIEF DESCRIPTION OF THE DRAWINGS

The accompanying drawings, which are incorporated in and constitute a part of this specification, illustrate systems and methods consistent with the invention and, together with the description, serve to explain the advantages and principles of the invention.

DETAILED DESCRIPTION

Reference will now be made in detail to an implementation consistent with the present invention as illustrated in the accompanying drawings. Wherever possible, the same reference numbers will be used throughout the drawings and the following description to refer to the same or like parts.

Ultrasound Navigation System Overview

Methods and systems consistent with the present invention permit physicians to navigate surgical probes more accurately without relying upon memorized models of the particular anatomy they may be operating upon. This is because the present system permits a physician to overlay ultrasound images over images from other image modalities giving the physician a three-dimensional image of the particular anatomy overlaid onto the ultrasound image relevant to that anatomy. Overlaying of images along with correlation of points in images from different image modalities can also help the physician in detecting organ-matter shift.

Figure 1:
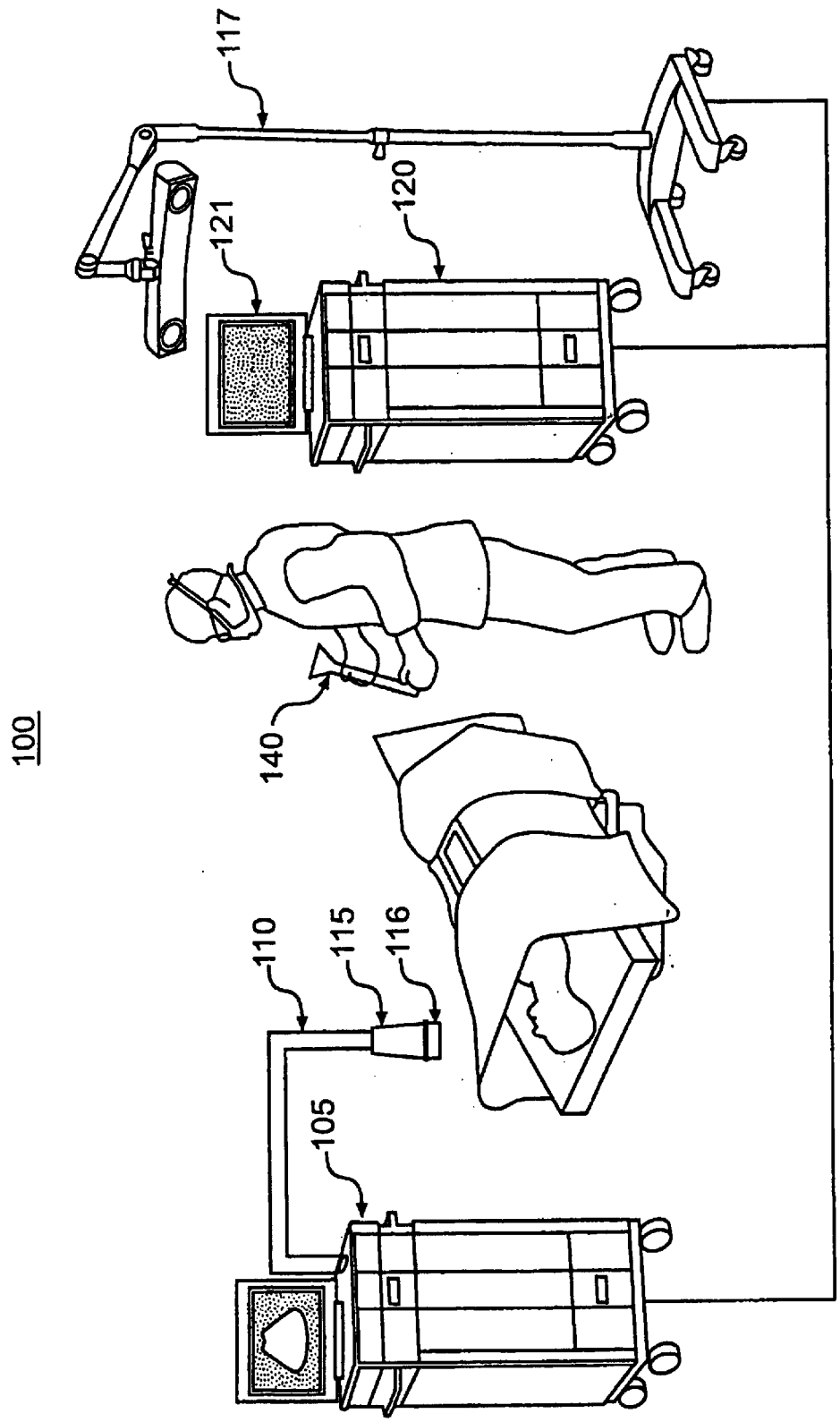
FIG. 1 is a diagram of an exemplary system used to overlay ultrasound images onto preacquired images from other image modalities.

FIG. 1 is a diagram of an exemplary ultrasound navigation system 100 used to acquire ultrasound images. Ultrasound machine 105 is a standard ultrasound machine capable of acquiring ultrasound images and displaying them on the built-in monitor. The ultrasound machine has a probe 115 attached to it via an arm 110, such that the ultrasound probe 115 can be manipulated by a physician to point it at the area of interest to the physician. For example, the physician can point the ultrasound probe 115, on the head of a patient to acquire ultrasound images corresponding to the head of that patient. The ultrasound probe 115 has a localizer 116, also referred to as a tracking marker, attached at its distal end. The localizer 116 can include optical, electromagnetic, acoustic device, or other suitable devices known in the prior art. Localization is a standard technique used in image guided surgery to locate the orientation and position of a surgical instrument or an ultrasound probe relative to a patient's position known in the art. For example, each of the following references discuss systems and methods that permit localization, each of which is incorporated by reference: PCT Publication WO 96/11624 to Bucholz et al., published Apr. 25, 1996; U.S. Pat. No. 5,384,454 to Bucholz; U.S. Pat. No. 5,851,183 to Bucholz; and U.S. Pat. No. 5,871,445 to Bucholz.

Referring further to FIG. 1, the ultrasound machine 105 is connected to a computer 120 such that the acquired ultrasound image data can be transferred to the computer 120. The computer 120 is connected to a display 121, such that images stored on a storage media can be digitally manipulated, saved, printed, or displayed on the display 121. Three-dimensional images, such as pre-acquired images obtained from computed tomography (CT) or Magnetic Resonance Imaging (MR) image data-sets for a particular patient, stored on a storage media, such as an external tape-drive, not shown, attached to the computer 120 may also be manipulated by computer 120 and displayed by the display 121. In addition, the images displayed on the display 121 may also be displayed through a head-mounted display worn by the physician.

Additionally, although FIG. 1 shows only one computer 120, one may have multiple computers implemented as a single computer to perform the functions performed by the computer 120. Moreover, one may not need external storage media for storing the images since those images could be stored on a remote server connected to the computer 120 through a local area network (LAN). In addition, even though FIG. 1 shows only one display 121 coupled to the computer 120, one may have multiple displays, including LCD displays, connected to the computer 120.

Moreover, even though FIG. 1 only illustrates the use of a patient specific CT/MR data-set, the disclosed system may also have three-dimensional atlas data-sets stored on the computer 120. For example, one may have a three-dimensional atlas data-set for the human brain or the kidney stored on a remote server accessible to the computer 120 through a LAN, or on the storage media attached to the computer 120. Atlas data is non-patient specific three-dimensional data describing a "generic" patient. Atlas data may be acquired using CT, MR or other imaging modalities from a particular patient; and may even comprise images from several modalities which are spatially registered (e.g., CT and MR together in a common coordinate system). Atlas data may also have annotations describing anatomy, physiology, pathology, or "optimal" planning information.

In addition, in general, the term "pre-acquired," as used herein, is not intended to imply any required minimum duration between the acquisition of image data-sets and displaying the corresponding images. Accordingly, a physician may "pre-acquire" image data-sets during surgery while operating upon a patient using the disclosed system.

To operate upon a patient using the disclosed ultrasound surgical navigation system, the patient is positioned between the ultrasound probe 115 and the tracking sensor 117.

A surgical instrument 140 is also embedded with tracking markers, such as for example, emitters and/or reflectors. These markers permit determination of the three dimensional position of an object relative to a patient. The determination of the three dimensional position of an object relative to a patient is known in the art. As mentioned earlier, each of the Bucholz references discuss systems and methods for determination of the three dimensional position of an object relative to a patient. Using known systems in the prior art, the disclosed system can locate the position and orientation of a surgical instrument or a probe being used to operate upon the patient.

Ultrasound Navigation System Setup and Operation

Figure 2:
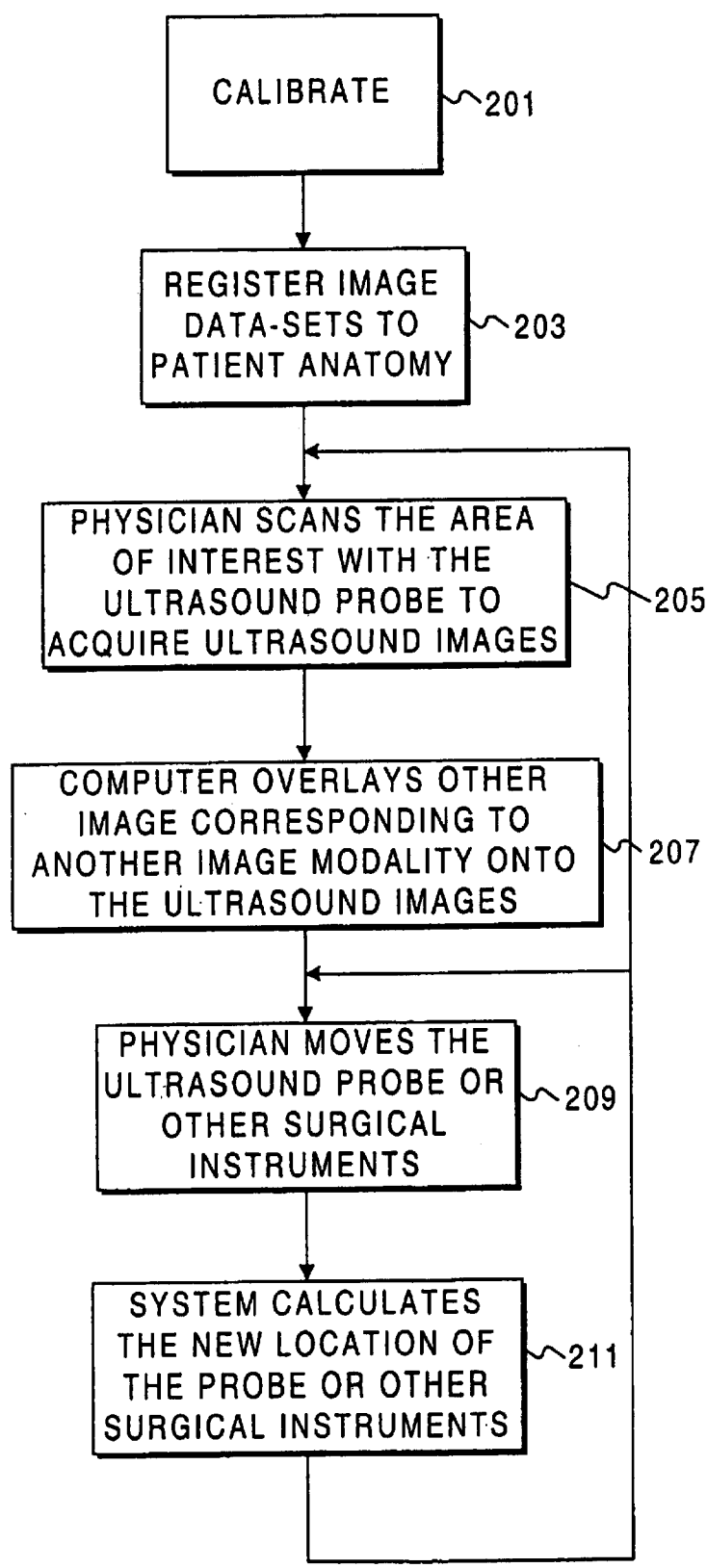
FIG. 2 is a flow chart illustrating methods consistent with the present invention for navigation using overlaid images.

FIG. 2 is a flow chart illustrating the steps for methods consistent with the present invention for ultrasound navigational guidance using the system of FIG. 1. As shown, there are six main steps involved in using the ultrasound navigational guidance system. A physician needs to initially perform the first step, Calibrate 201. After calibrating, discussed hereinafter, in the second step 203, the pre-acquired data-sets belonging to other image modalities may need to be registered in order to obtain a correspondence between these images and the real-time ultrasound images. This step, discussed in detail later, need not be performed every time. Subsequently, in step 205 the physician scans the area of interest of the human anatomy with the ultrasound probe 115. For example, the physician may scan the brain of a patient to obtain ultrasound images of the brain. Next, in step 207 the computer overlays the pre-acquired images corresponding to other image modalities, such as CT and MR onto the ultrasound images. Later, in step 209 the physician may move the surgical instruments or the ultrasound probe. Finally, in the sixth step 211, the system can calculate and display the new position and orientation of the surgical instruments or the ultrasound probe on different images and also on three-dimensional images overlaid on the real-time ultrasound images.

During surgery, the physician may go back to step 205 and scan another area of interest and accordingly the computer may overlay pre-acquired images belonging to other image modalities onto the new ultrasound images. Alternatively, the physician may simply move the ultrasound probe 115 or other surgical instruments as per step 209, and yet remain within the earlier scanned area of interest. Consequently, the system calculates the new location of the ultrasound probe 115 or other surgical instruments and displays the overlapping images on the display 121 attached to the system.

Referring to FIG. 2, as discussed above, a physician or her assistant calibrates the navigational guidance system before using the system for the first time (step 201). In addition, the physician may need to calibrate the system later occasionally to improve the system's accuracy. Indeed, calibration may be performed by service technician familiar with the navigational guidance system. Calibration is the process used to precisely calculate the location of the ultrasound image plane relative to the localizer 116.

Calibration of image guided surgical devices is known in the art. In addition, a U.S. Pat. No. 6,470,207, issued Oct. 22, 2002, assigned to the same assignee, describes calibration in the context of a navigational guidance system using x-rays, which is incorporated by reference. In general, calibration consists of using a calibration device, which may contain objects, such as rows and columns of wires, inside a frame, that can be detected by an ultrasound machine. A user scans the calibration device with the ultrasound probe 115 and the attached localizer 116. The ultrasound navigation system with the help of software running on the computer 120 locates the intersection of wires, which appear as dots in the scanned image of the calibration device. The computer 120 then calculates a transformation between these dots and the actual intersection of the wires that formed a dot located on the actual calibration device.

As discussed earlier, a physician, or the physician's assistant, may use Computed Tomography (CT). or Magnetic Resonance Imaging (MRI) to acquire CT or MR data-sets corresponding to each one of these image modalities. These pre-acquired image data-sets can be stored on a storage device coupled to the computer 120. In addition, these three-dimensional data sets may be acquired by the physician during the operation. Furthermore, the present invention is not limited to using CT or MR images. One may use images from other image modalities as well with the present invention. For example, images acquired using other diagnostic tools, such as Positron Emission Tomography (PET) or X-rays may also be used.

With the ultrasound navigation system setup and the data-sets corresponding to other image modalities acquired, the physician may in step 205 begin surgery by scanning the specific area of human anatomy which needs operative care with the ultrasound probe 115. The real-time image of the specific area acquired by the ultrasound probe 115 is displayed on the display which is part of the ultrasound machine. Next, upon the physician's command the system overlays the three-dimensional image corresponding to a different image modality data-set onto the ultrasound image along with an iconic representation of the surgical instrument 140.

However, before overlaying the three-dimensional image with a graphical representation of a surgical instrument, the correspondence between points in the three-dimensional image and points in the patient's reference frame may need to be determined in step 203, as shown in FIG. 2. The process to achieve this correspondence is known as registration of the image. One method for performing image registration is described in the previously mentioned publications to Bucholz. Another method for performing image registration is described in U.S. Pat. No. 6,470,207, issued Oct. 22, 2002, to the same assignee.

In general, three-dimensional patient specific images can be registered to a patient on the operating room table (surgical space) using multiple two-dimensional image projections. This process, generally referred to as 2D/3D registration, uses two pre-established spatial transformations to relate the surgical space to the three-dimensional image space. Accordingly, the first transformation is between the ultrasound images and the three-dimensional image data-set, such as a CT or an MR data-set corresponding to the same patient.

The second transformation is between the coordinate system of the ultrasound images and an externally measurable reference system, which can be achieved using a tracking sensor 117. Tracking sensor 117 is a real-time infrared tracking sensor linked to computer 120. Specially constructed surgical instruments and other markers, also known as localizers, in the field of tracking sensor 117 can be detected and located in three-dimensional space. For example, a surgical instrument 140, such as a drill, may be embedded with tracking elements, such as for example, infrared emitters/reflectors on its handle. Tracking sensor 117 can then detect the presence and location of infrared emitters/reflectors. Because the relative spatial locations of the emitters/reflectors in instrument 140 are known a priori, tracking sensor 117 and computer 120 are able to locate instrument 140 in three-dimensional space using known mathematical transformations. Instead of using infrared tracking sensor 117 and corresponding infrared emitters/reflectors, other types of positional location devices are known in the art, and may be used. For example, a positional location device may also be based on magnetic fields, optic emissions, sonic emissions, or radio waves. Once these two transformations have been established, the system may relate the surgical space directly to the three-dimensional image space.

Finally, with a display of the surgical instrument overlaid on the ultrasound image, which in turn is blended with a three-dimensional image from another modality the physician can guide the surgical instrument more effectively. Several well known techniques can be used to blend the images. For example, a computer may implement an algorithm that for each pixel establishes $\alpha$ as the blending ratio. Assuming X is a pixel from the ultrasound image and Y is a pixel from the MR or CT image. Then the computer may perform the following calculation to arrive at a pixel Z for the blended image:

$$\text{Blended Image Pixel } Z=((X^*\alpha)+(Y^*(1-\alpha)))$$

Figure 5:
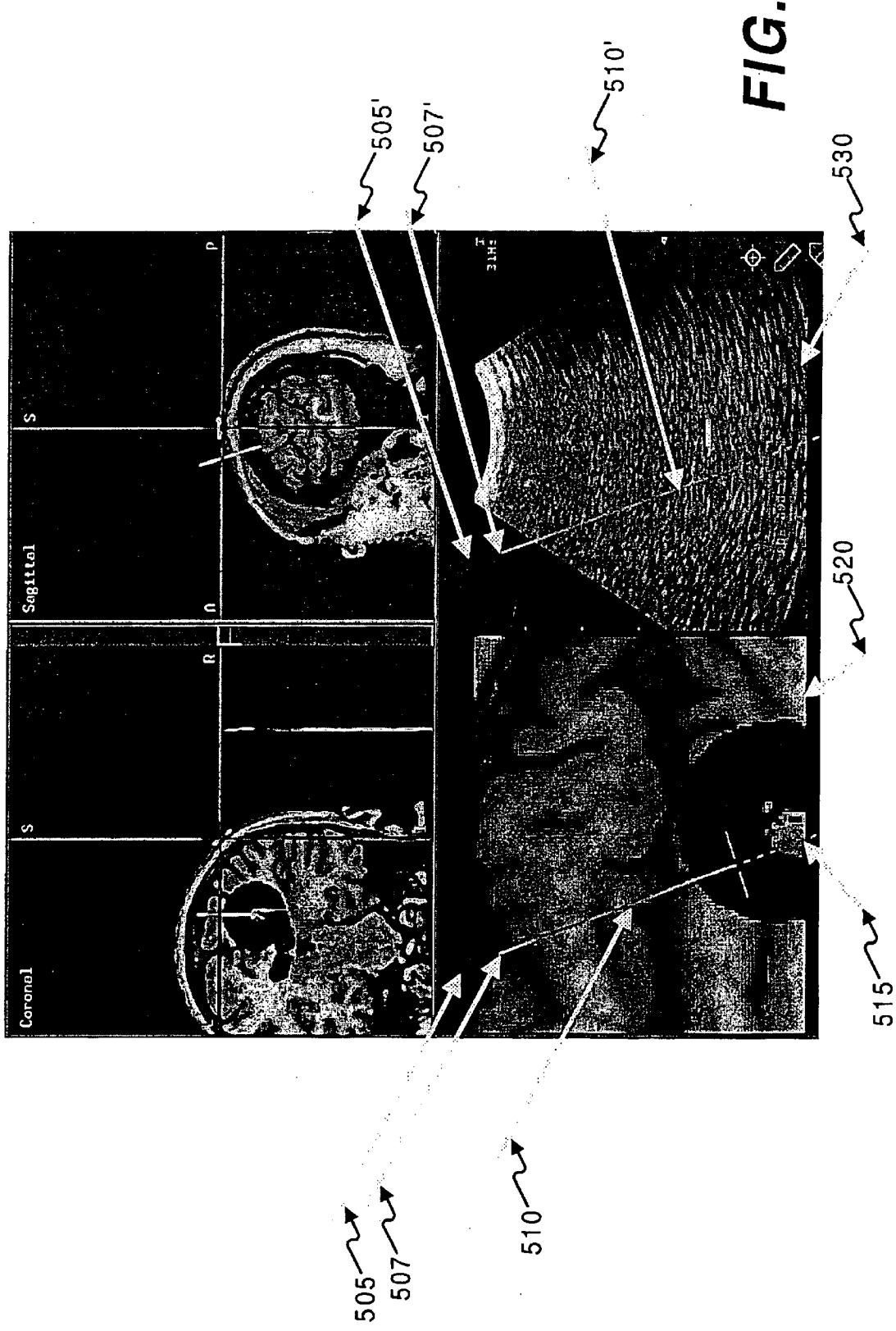
FIG. 5 is a pictorial image showing an MR data-set image and an ultrasound image side by side on a display consistent with the present invention.

Referring to FIGS. 1 and 5, when during surgery the physician moves the ultrasound probe 115 or other surgical instrument(s) in step 509, the system calculates the new location of the ultrasound probe 115 or the location of other surgical instruments. The system does this by using a technique called localization, which as discussed earlier, is known in the art.

In addition to above methods and techniques a physician may achieve better surgical navigation using the techniques and methods discussed below.

Displaying Surgical Instrument to Ultrasound Image Angle

Figure 3:
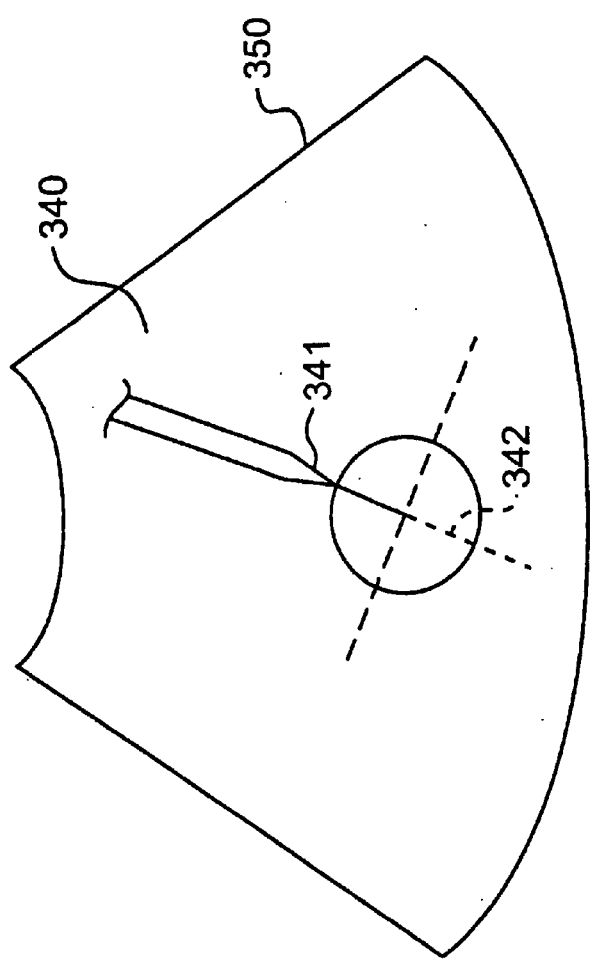
FIG. 3 is a diagram illustrating a method consistent with the present invention for measuring the angle of a surgical instrument's trajectory relative to an ultrasound image plane.
Figure 4:
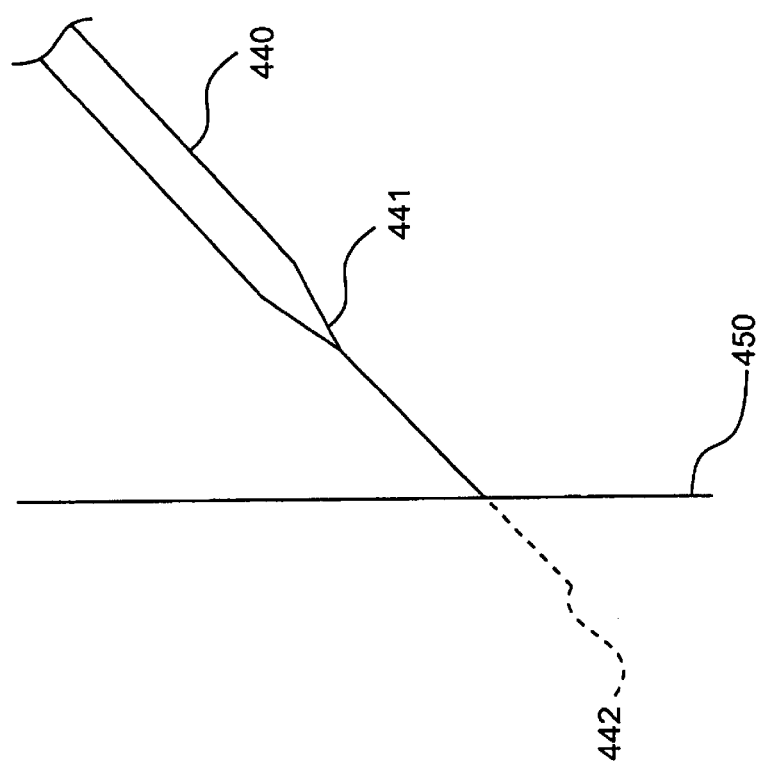
FIG. 4 is a diagram showing a display of a side view of an ultrasound image with an iconic representation of a surgical instrument and its trajectory indicating the angle of the surgical instrument relative to the ultrasound probe.

Referring to FIGS. 1, 3, and 4 the ultrasound navigation system may also be used to calculate and display the angle of a surgical instrument 340 to the ultrasound image plane 350. The computer 120 may calculate the angle by drawing a circle with its center at the point where the surgical instrument's trajectory 342 passes through the ultrasound image plane 350. The radius of the circle may represent the angle of the trajectory 342 to the ultrasound plane 350. This is because the computer 120 may use trigonometric techniques such as drawing a perpendicular line from the tip 341 of the surgical instrument 340 onto the ultrasound image plane 350. Accordingly, the radius of a circle drawn by the computer 120 with its center at the point where the surgical instrument's trajectory 342 passes through the ultrasound image plane 350 may represent the angle of the surgical instrument 340 to the ultrasound image plane 350. The system may display this angle on the display 121 as shown in FIG. 4.

Referring to FIG. 4, the system may display a side view of the ultrasound image plane 450. It may also display the trajectory of a surgical instrument 440 intersecting with the ultrasound image plane 450 and changing the display of the trajectory to a dotted representation 442 after the trajectory crosses the ultrasound image plane 450.

Figure 6:
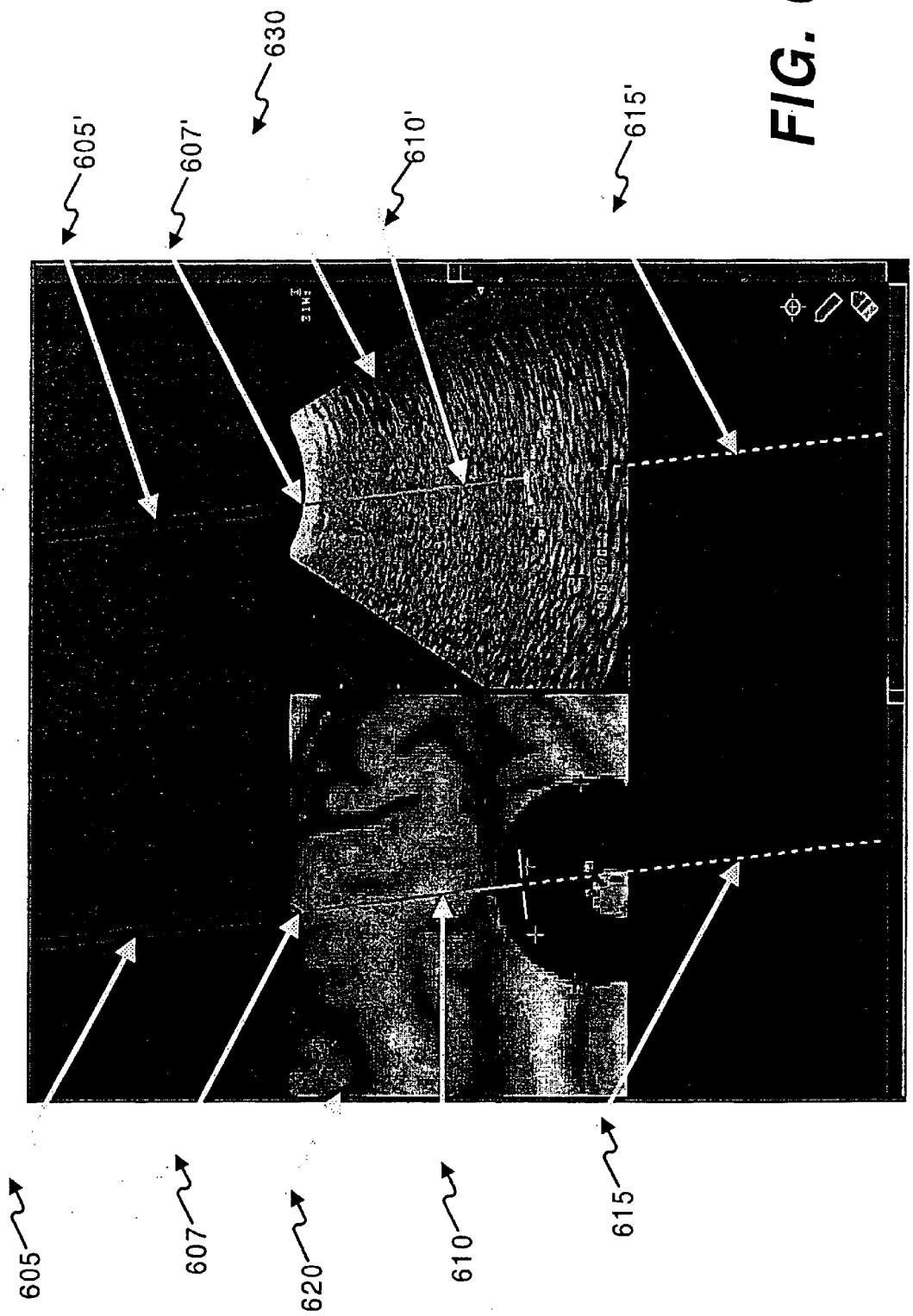
FIG. 6 is a pictorial image representing a closer view of the MR image and the ultrasound image.

FIG. 5 is a pictorial image showing an MR data-set image 515 and an ultrasound image 530 side by side on the display 120. Both images have an iconic representation of a surgical instrument 505 superimposed on the images. The figure also indicates that the system displays a trajectory of a surgical instrument tip 507 and changes the trajectory from a solid line trajectory 510 to a dashed line trajectory 515 when the trajectory crosses the MR data-set image plane and the ultrasound image plane respectively. FIG. 6 is another pictorial image representing a zoomed-in view of the MR image and the ultrasound image. A physician may select either view or may display both views on the display 121.

Figure 7:
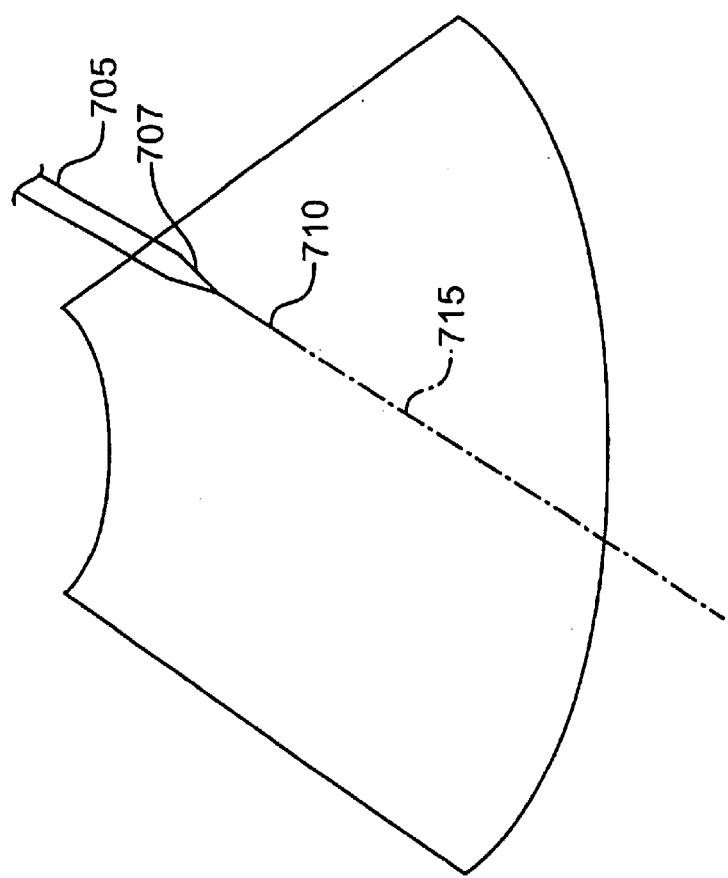
FIG. 7 is a diagram illustrating a method consistent with the present invention for displaying the angle of an ultrasound probe relative to an ultrasound image plane.

Displaying Surgical Instrument to Ultrasound Image Angle Using Periodic Markers Referring to FIG. 7, the disclosed system can display the angle of the surgical instrument 140 relative to the ultrasound image plane by displaying periodic markers 715. The distance between the periodic markers changes as a function of the cosine of the angle between the surgical instrument trajectory 710 and the ultrasound image plane. Accordingly, the periodic markers may also indicate the angle of the surgical instrument trajectory 710 to the ultrasound image.

Displaying Orthogonal Images for Better Navigation

Figure 8:
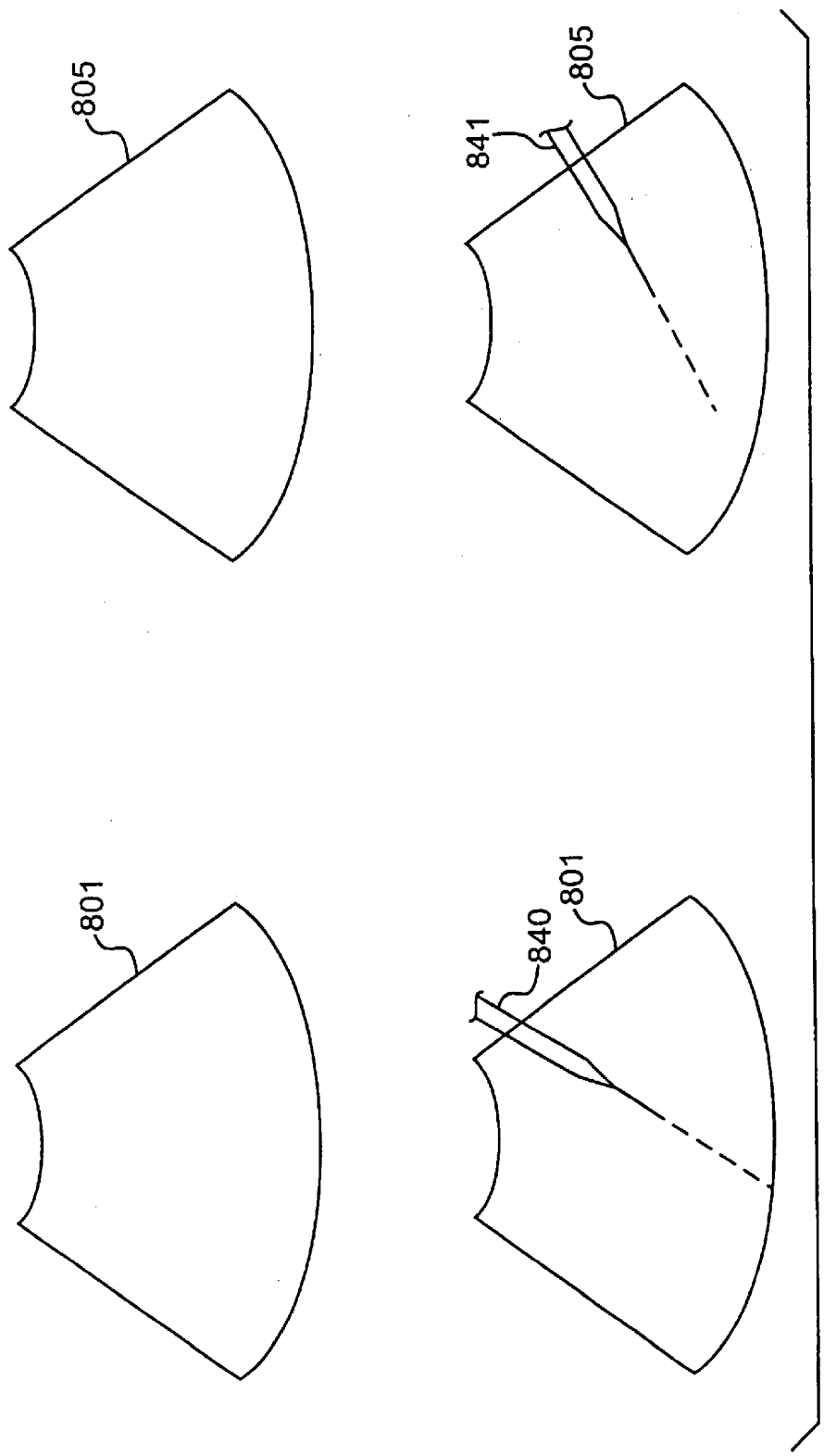
FIG. 8 is a diagram illustrating the use of orthogonal ultrasound images in surgical navigation consistent with the present invention.

Referring to FIG. 8, the ultrasound navigation system may also display multiple orthogonal ultrasound images 801 and 805. In addition, the system may also upon command display iconic representation 840 of a surgical instrument onto the orthogonal ultrasound images 801 and 805.

Overlaying Segmentations onto Ultrasound Images

The system disclosed in FIG. 1, may also be used to overlay image segmentations onto ultrasound images for surgical navigation. In general, segmentations are surfaces or sets of other information extracted from a three-dimensional data-set. Segmentations can be obtained by the computer 120, on command, from the pre-acquired three-dimensional image data-sets by using known computer graphics algorithms. The extracted segmentation can then be overlaid onto an ultrasound image in the correct perspective by the computer 120. The overlaid image can be displayed by the display 121, as discussed earlier.

In addition, referring to FIG. 1, and as discussed earlier, the computer 120 also displays an iconic representation of any surgical instrument 140 with tracking sensors. Also, the computer 120 can recalculate and display the location of the surgical instrument 140 onto the overlaid image when the physician moves the surgical instrument 140 during surgical navigation.

Surgical Navigation with Three-Dimensional Image Data-Sets

The ultrasound navigation system shown in FIG. 1 may also be used to help a physician in surgical navigation by displaying three-dimensional ultrasound image data-sets. A physician or a physician's assistant can acquire a three-dimensional ultrasound image data-set by using known techniques that may be free-hand or may involve use of mechanical movements. Once the image data is acquired using any of the known techniques, the computer 120 can then using graphics related mathematical computations reconstruct this data into an orthogonal data-set. Later, the computer 120 can display the orthogonal data-set as a three-dimensional image on the display 121.

The computer 120 then overlays a real-time ultrasound image over the pre-acquired and computationally generated three-dimensional image in the right perspective. In addition, the computer 120 with the help of known algorithms can map an ultrasound image relating to an area of an interest onto the surface of the pre-acquired three-dimensional image of the same area. The general technique of mapping an image onto the surface of a three-dimensional image in the correct perspective is known in the art, and is referred to as texture mapping. Accordingly, using known texture mapping algorithms, an ultrasound image of an area of interest can be mapped onto a three-dimensional image of a particular area of human anatomy, and can be displayed on the display 121, aiding a physician in better surgical navigation.

In general; however, due to perspective transformation or the curvature of the surface, texture mapping may result in a distorted image. To alleviate this problem, the disclosed system may use known filtering-techniques that help reduce distortion. Thus, the computer 120 with the help of software can execute instructions corresponding to known filtering algorithms, which can reduce image distortion.

In addition, referring to FIG. 1, and as discussed earlier, the computer 120 also displays an iconic representation of any surgical instrument 140 with tracking sensors. Also, the computer 120 can recalculate and display the location of the surgical instrument 140 onto the texture mapped ultrasound image when the physician moves the surgical instrument 140 during surgical navigation.

Detecting Organ Shift Using the Ultrasound Navigation System

Figure 9:
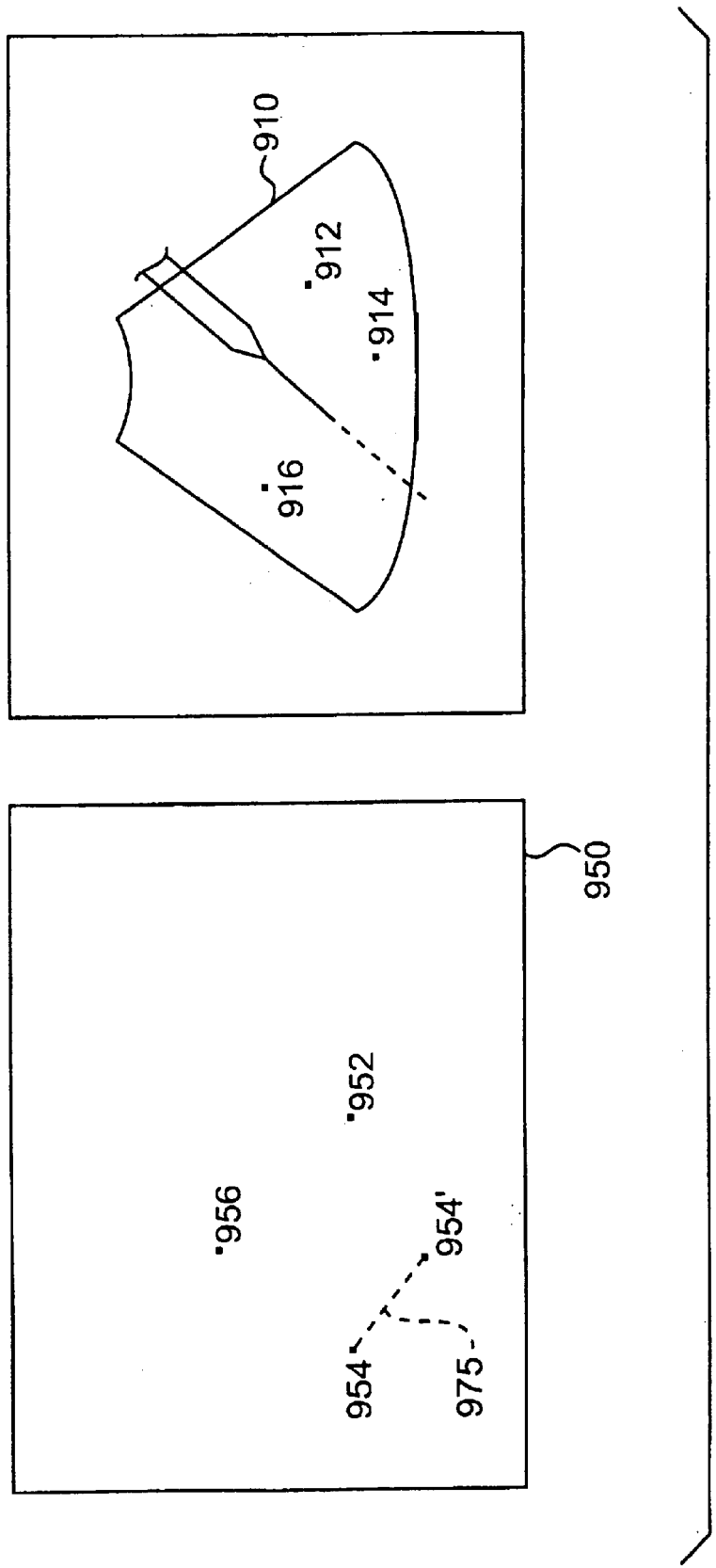
FIG. 9 is a diagram illustrating a method consistent with the present invention for detecting shift in organ matter.

The ultrasound navigation system shown in FIG. 1 may also be used to detect organ-matter shift during surgery. Detection of organ-matter shift is important since a patient's organ-matter may have shifted from the time when CT or MR data-sets for that patient were created to the time when the patient is actually operated upon. For example, a physician's assistant may have obtained CT or MR images of a patient needing neurosurgery. However, the physician scheduled to operate upon the patient may not operate upon the patient until a later time during which the grey-matter or other organic matter comprising the brain may have shifted. Referring to FIG. 9, once the ultrasound image 910 and the extracted CT or MR two-dimensional image 950 are correlated the computer 120 with the help of software can perform certain calculations and measurements to indicate organ-matter shift.

Correlation involves performing registration, localization, and calibration. Registration, as discussed earlier, involves determining the correspondence between points in the three-dimensional image and points in the patient's reference frame. One method for performing image registration is described in the previously mentioned publications to Bucholz. Another method for performing image registration is described in U.S. Pat. No. 6,470,207, issued Oct. 22, 2002, to the same assignee.

In general, as discussed earlier, three-dimensional patient specific images can be registered to a patient on the operating room table (surgical space) using multiple two-dimensional image projections. This process, generally referred to as 2D/3D registration, uses two pre-established spatial transformations to relate the surgical space to the three-dimensional image space. Accordingly, the first transformation is between the ultrasound images and the three-dimensional image data-set, such as a CT or an MR data-set corresponding to the same patient. The second transformation is between the coordinate system of the ultrasound images and an externally measurable reference system which can be achieved using a tracking sensor 117. The tracking sensor 117 is also known as a localizer array, and the process of achieving the previously mentioned transformation is referred to as localization.

Tracking sensor 117 is a real-time infrared tracking sensor linked to computer 120. Specially constructed surgical instruments and other markers in the field of tracking sensor 117 can be detected and located in three-dimensional space. For example, a surgical instrument 140, such as a drill, is embedded with infrared emitters/reflectors on its handle. Tracking sensor 117 detects the presence and location of infrared emitters/reflectors. Because the relative spatial locations of the emitters/reflectors in instrument 140 are known a priori, tracking sensor 117 and computer 120 are able to locate instrument 140 in three-dimensional space using well known mathematical transformations. Instead of using infrared tracking sensor 117 and corresponding infrared emitters/reflectors, other types of positional location devices are known in the art, and may be used. For example, a positional location device may also be based on magnetic fields, sonic emissions, or radio waves. Once these two transformations have been established, the system may relate the surgical space directly to the three-dimensional image space.

Finally, the system may need to be calibrated. Calibration is the process to precisely calculate the location of the ultrasound image plane relative to the localizer 116. Consequently, calibration improves the interpretation of the ultrasound images where the ultrasound probe 115 may have been displaced in relation to the localizer 116.

As discussed earlier, calibration of image guided surgical devices is known in the art. For example, the previously mentioned Bucholz references describe calibration. In addition, U.S. Pat. No. 6,470,207, issued Oct. 22, 2002, assigned to the same assignee, describes calibration in the context of a navigational guidance system using x-rays. In general calibration consists of using a calibration device, which may contain objects, such as rows and columns of wires inside a frame, that can be detected by an ultrasound machine. A user scans the calibration device with the ultrasound probe 115 and the attached localizer 116. The ultrasound navigation system with the help of software running on the computer 120 locates the intersection of wires, which appear as dots in the scanned image of the calibration device. The computer 120 then calculates a transformation between these dots and the actual intersection of the wires that formed a dot located on the actual calibration device.

Once the system disclosed in FIG. 1 has registered, calibrated, and localized the images, the system may be used to detect organ-matter shift using certain measurements. To perform these measurements, points 912, 914, and 916 must first be established within the ultrasound image 910. These points may be established using any peripheral device attached to the computer 120. For example, a mouse attached to the computer 120 may be used to select the points of interest on the ultrasound image 910.

Once these points are selected the software on computer 120 can then transform the coordinates of these points into a three-dimensional image generated from CT or MR data-set specific to a patient. Next, the software running on computer 120 can extract the correlated CT or MR two-dimensional image from the three-dimensional CT or MR data-set. Having done so, the computer 120 can display the extracted two-dimensional image on the display 121.

The physician can then select points 952, 954, and 956 on the extracted two-dimensional image 950 corresponding to the ultrasound image 910 by finding the corresponding anatomy in the extracted two-dimensional image 950. The computer 120 can then display the distance and the trajectory 975 between the corresponding points, giving the physician a graphical view of the extent of the organ-matter shift. For example, referring to FIG. 6, the dotted line 975 represents the organ-matter shift as indicated by the distance between point 954 and point 954', which is where the corresponding point to 914 would have appeared had the organ-matter not shifted.

Overlay of Video Imagery onto Ultrasound Images

Figure 10:
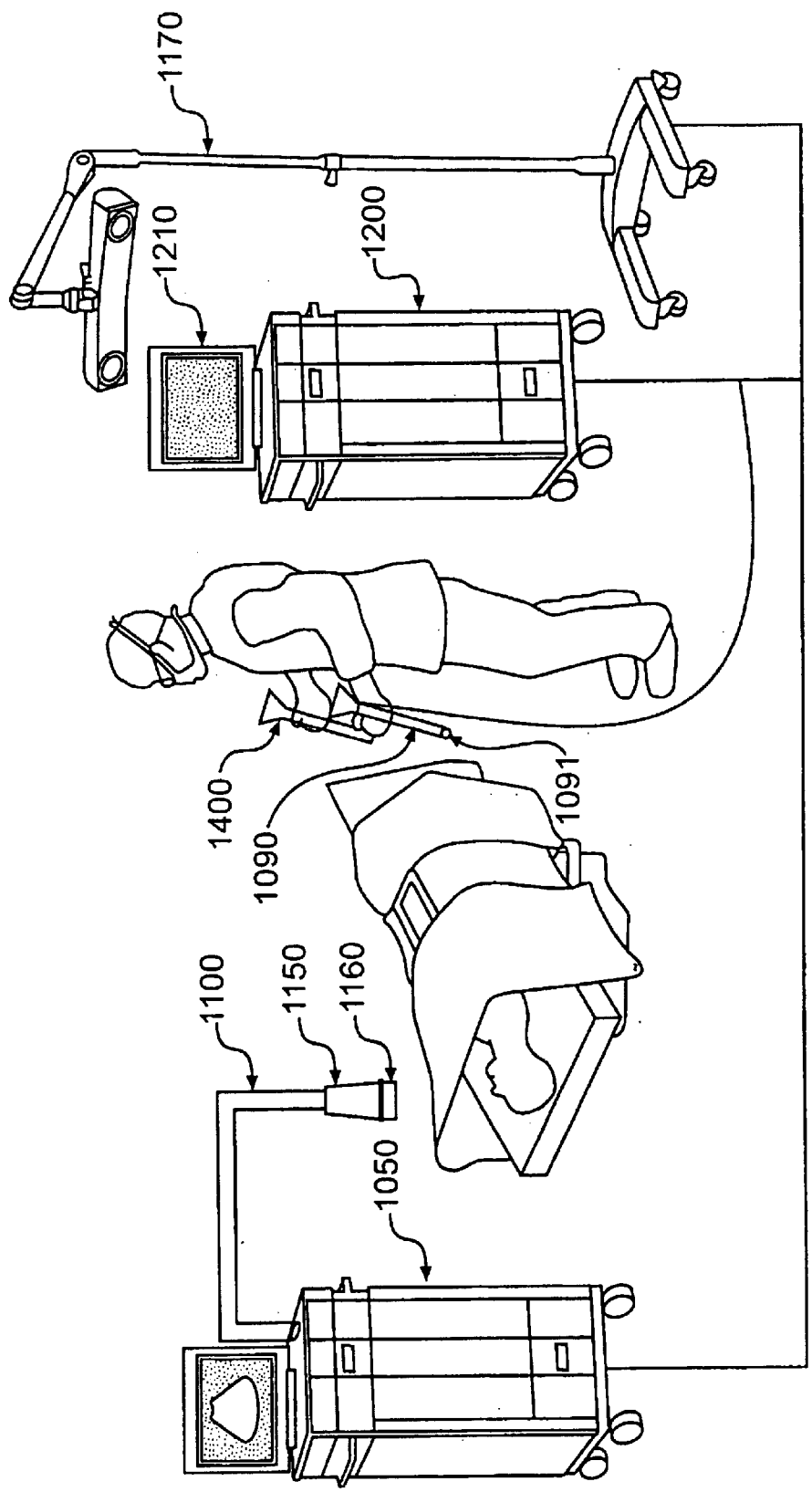
FIG. 10 is a diagram of an exemplary system used to overlay ultrasound images onto video images acquired using a laparoscope or an X-ray machine.

Referring to FIG. 10, an ultrasound machine 1050 is connected to a computer 1200 such that the acquired ultrasound images can be transferred to the computer 1200. The computer 1200 is connected to a display 1210, such that images stored on a storage media can be digitally manipulated, saved, printed or displayed on the display 1210. Also, an X-ray machine or a laparoscope 1090 may also be connected to the computer such that X-ray images or video imagery from the laparoscope 1090 can be transferred to the computer 1200. In addition, like the ultrasound images, these images can also be digitally manipulated, saved, printed, or displayed on the display 1210.

Referring to FIG. 10, both the ultrasound machine 1050 and the laparoscope 1090 have each a localizer 1160, 1091 attached to them. As discussed earlier, the localizers could be, for example, either optical, electromagnetic, acoustic, or other known systems. In addition, localization is a standard technique used in image guided surgery to locate the orientation and the position of a surgical instrument, an ultrasound probe, or a laparoscope, relative to a patient's position and is known in the art. As mentioned earlier, each of the Bucholz references discuss systems and methods that permit localization.

Figure 11:
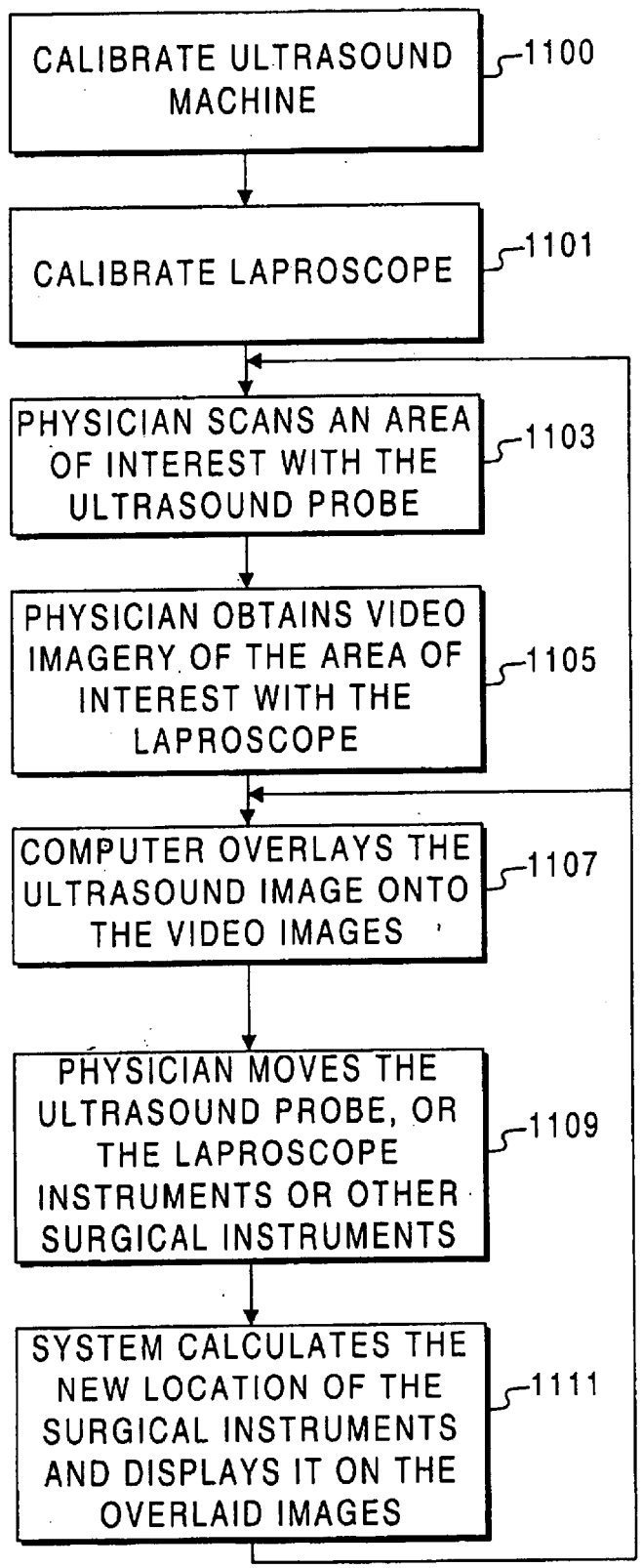
FIG. 11 is a flow chart illustrating methods consistent with the present invention for navigation using overlaid ultrasound and video images.

FIG. 11 is a flow chart illustrating the steps for methods consistent with the present invention for ultrasound and video navigational guidance using the system of FIG. 10. As shown in FIG. 11, there are seven main steps involved in using the disclosed system. A physician needs to perform the first two steps: Calibrate ultrasound machine (step 1100) and Calibrate laparoscope (step 1101), only occasionally. After calibration, which need not be performed every time, the physician in the third step, step 1103, scans an area of interest of human anatomy using the ultrasound probe. Subsequently, in step 1105 the physician obtains a video image of the same area of that particular patient using a laparoscope 1090. Note that the physician may in this step use an X-ray machine to acquire an image of the same area of anatomy as well. In general, a physician may use any known system that permits the physician to obtain a video image of the relevant area of interest.

Later, in step 1107, the computer overlays the acquired ultrasound image onto the video image. For the images to be useful in surgical navigation the system ensures that the ultrasound probe 1150 and the laparoscope 1090 are localized. As discussed earlier, localization is a known technique. In the next step 1109, the physician during surgery may move the ultrasound probe 1150, or the laparoscope 1090. In addition, the physician may be using a surgical instrument 1400, which also has been localized, to perform the surgery. In step 1111, the system calculates the new location of the surgical instrument 1400 and displays it on the overlaid images. If the physician, scans a different area of interest, then the system displays the overlaid images corresponding to the new area of interest. In addition, the system calculates the new location of the surgical instrument 1400 and displays an iconic representation of the surgical instrument 1400 on the display 1210.

Figure 12:
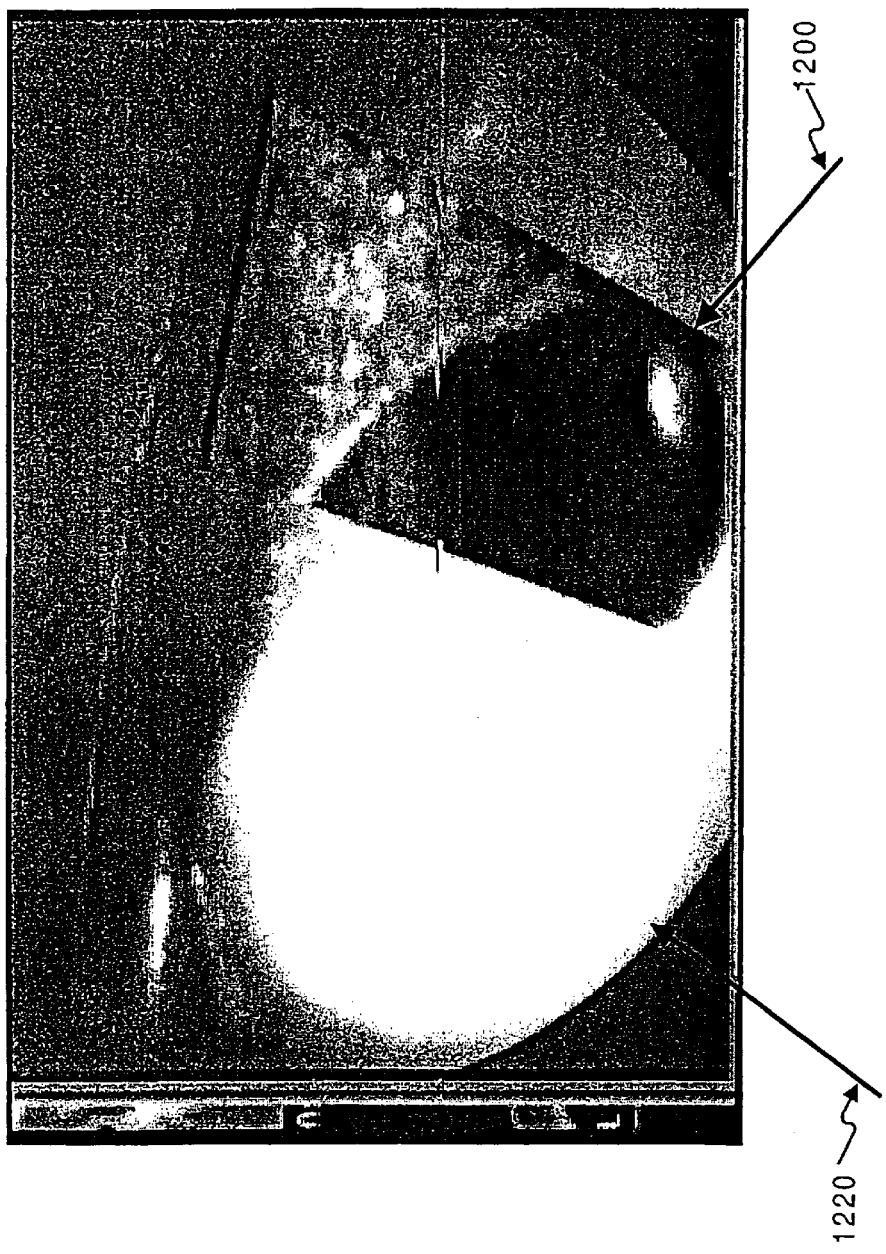
FIGS. 12 and 13 are pictorial images representing two video laparoscope images of a gallbladder with an ultrasound image overlaid in correct perspective.
Figure 13:
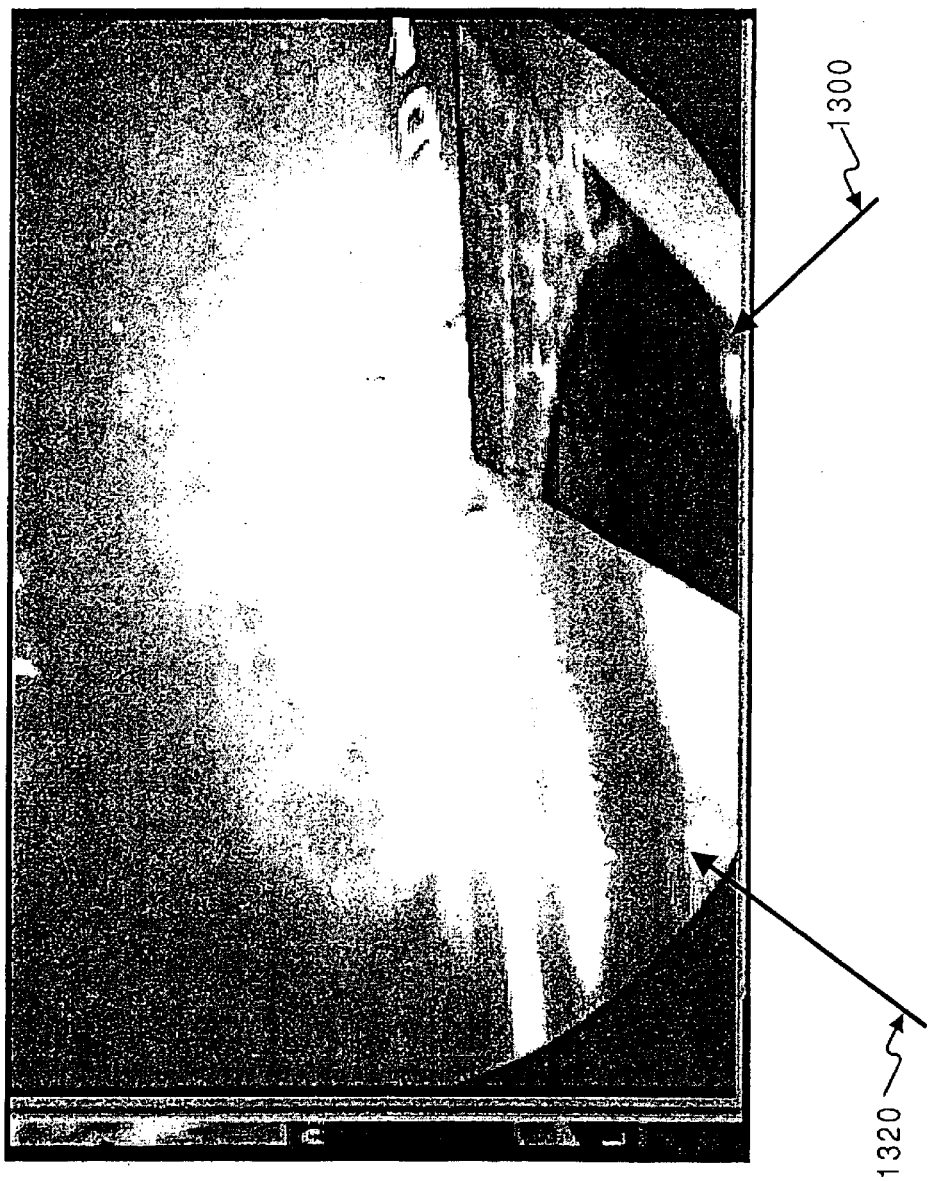

FIGS. 12 and 13 are pictorial images representing the two video laparoscope images 1220 and 1320 of a gallbladder with an ultrasound image 1200/1300 overlaid in correct perspective.

What is claimed is:

1. A method for detecting organ-matter shift in a patient, the method comprising:
   pre-acquiring a three-dimensional image data set of the patient;

obtaining a real-time ultrasound image of the patient;

correlating the real-time ultrasound image and the preacquired three-dimensional image to obtain a correlated two-dimensional image;

selecting a first set of points on the real-time ultrasound image;

selecting a corresponding second set of points on the correlated two-dimensional image; and determining a vector representing at least one of a distance and a direction of the organ matter shift.

2. The method as defined in claim 1 further comprising displaying the vector representing at least one of a distance and a direction of the organ matter shift.

3. The method as defined in claim 2 further comprising displaying the vector on the correlated two-dimensional image.

4. The method as defined in claim 3 further comprising displaying the vector as a dotted line on the correlated two-dimensional image.

5. The method as defined in claim 1 wherein preacquiring a three-dimensional image data set of the patient further includes preacquiring a three-dimensional atlas data set.

6. The method as defined in claim 1 further comprising overlaying image segmentations onto the real-time ultrasound image of the patient.

7. The method as defined in claim 1 wherein selecting a first set of points includes selecting three points on the real-time ultrasound image and selecting a corresponding second set of points includes selecting three corresponding points on the correlated two-dimensional image.

8. The method as defined in claim 1 wherein pre-acquiring the three-dimensional image of the patient is acquired by using an imaging device selected from a group consisting of ultrasound, computed tomography (CT), magnetic resonance imaging (MRI), positron emission tomography (PET), x-rays or any combination thereof.

9. The method as defined in claim 8 further comprising tracking a location of a surgical instrument using the position tracking sensor.

10. The method as defined in claim 1 wherein correlating the real-time ultrasound image and the pre-acquired three-dimensional image includes performing at least one of registration, localization, and calibration.

11. The method as defined in claim 10 wherein the registration is 2-D/3-D registration that uses two pre-established spatial transformations to relate surgical space to a pre-acquired three-dimensional image space.

12. The method as defined in claim 11 wherein the first transformation is between the real-time ultrasound image and the pre-acquired three-dimensional image data set and the second transformation is between a coordinate system of the ultrasound image and an externally measurable reference system using a position tracking sensor.

13. The method as defined in claim 12 wherein said position tracking sensor is selected from a group consisting of optical, electromagnetic, acoustic localizers, or any combination thereof.

14. The method as defined in claim 1 wherein the organ-matter shift is a brain shift.

15. The method as defined in claim 14 further comprising calibrating a tracked ultrasound image device that is operable to obtain the real-time ultrasound image of the patient.

16. The method as defined in claim 15 wherein the calibration further includes scanning a calibration device with the tracked ultrasound image device and calculating a transformation between landmarks identified by the ultrasound image device and the actual landmarks on the calibration device.

17. The method as defined in claim 16 further comprising generating the three-dimensional image data set from a device selected from a group consisting of ultrasound, computed tomography (CT), magnetic resonance imaging (MRI), positron emission tomography (PET), x-rays or any combination thereof.

18. The method as defined in claim 1 wherein selecting a first set of points in the real-time ultrasound image further includes selecting the points using a peripheral device.

19. The method as defined in claim 1 wherein correlating the real-time ultrasound image and the preacquired three-dimensional image further includes transforming coordinates of the first set of points selected on the real-time ultrasound image into the three-dimensional image data set to obtain the correlated two-dimensional image.

20. A method for surgical navigation using a surgical navigation system comprising:

extracting a two-dimensional image from a three-dimensional image data set;

overlaying the extracted two-dimensional image onto an ultrasound image; and displaying the overlaid image with an iconic representation of a localized surgical instrument superimposed on the overlaid image.

21. The method as defined in claim 20 further comprising:

moving the localized surgical instrument to a new location; and displaying an iconic representation of the new location of the surgical instrument on the overlaid image.

22. A method for surgical navigation using three-dimensional image data sets comprising:

acquiring a three-dimensional image data set;

reconstructing the three-dimensional image data set into an orthogonal data set;

displaying the orthogonal data set as a three-dimensional image on a display;

acquiring an ultrasound image and mapping the ultrasound image onto a surface of the three-dimensional image using textured mapping; and displaying the textured map image.

23. The method as defined in claim 22 further comprising displaying an iconic representation of a localized surgical instrument onto the textured map image.

24. The method as defined in claim 23 further comprising:

moving the localized surgical instrument to a new location; and displaying an iconic representation of the new location of the surgical instrument on the textured map image.

25. A method for detecting organ-matter shift in a patient, the method comprising:

pre-acquiring a three-dimensional image data set of the patient;

obtaining a real-time ultrasound image of the patient;

correlating the real-time ultrasound image and the preacquired three-dimensional image to obtain a correlated two-dimensional image using 2-D/3-D registration; and determining a vector representing at least one of a distance and a direction of the organ matter shift.

26. The method as defined in claim 25 further comprising displaying the vector representing at least one of a distance and a direction of the organ matter shift.

27. The method as defined in claim 25 wherein preacquiring a three-dimensional image data set of the patient further includes preacquiring a three-dimensional atlas data set.

28. The method as defined in claim 25 further comprising overlaying image segmentations onto the real-time ultrasound image of the patient.

29. The method as defined in claim 25 wherein correlating using 2-D/3-D registration further includes determining two spatial transformations to relate surgical space to three-dimensional image space.

30. The method as defined in claim 25 wherein using the two spatial transformations include using a first transformation between the ultrasound image and the three-dimensional image data set and using a second transformation between a coordinate system of the ultrasound image and an externally measurable reference system using a position tracking sensor.

31. The method as defined in claim 30 wherein said position tracking sensor is selected from a group consisting of optical, electromagnetic, acoustic localizers, or any combination thereof.

32. The method as defined in claim 30 further comprising tracking a location of a surgical instrument using the position tracking sensor.

33. The method as defined in claim 25 further comprising selecting a first set of points on the real-time ultrasound image and selecting a corresponding second set of points on the correlated two-dimensional image.

34. A method for detecting organ-matter shift from a preacquired three-dimensional image data set of a patient, the method comprising:

obtaining a real-time ultrasound image of the patient;

selecting a first set of points on the real-time ultrasound image;

transforming the coordinates of the first set of points into the preacquired three-dimensional image data set;

extracting a correlated two-dimensional image from the three-dimensional image data set;

selecting a corresponding second set of points on the correlated two-dimensional image; and determining a vector representing at least one of a distance and a direction of the organ matter shift.

35. The method as defined in claim 34 further comprising displaying the vector representing at least one of a distance and a direction of the organ matter shift.

36. The method as defined in claim 34 wherein preacquiring a three-dimensional image data set of the patient further includes preacquiring a three-dimensional atlas data set.

37. The method as defined in claim 34 further comprising overlaying image segmentations onto the real-time ultrasound image of the patient.

38. The method as defined in claim 34 wherein selecting a first set of points includes selecting three points on the real-time ultrasound image and selecting a corresponding second set of points includes selecting three corresponding points on the correlated two-dimensional image.

39. The method as defined in claim 34 further comprising tracking a location of a surgical instrument using a position tracking sensor.

40. The method as defined in claim 34 further comprising calibrating a tracked ultrasound image device that is operable to obtain the real-time ultrasound image of the patient.

41. The method as defined in claim 34 wherein selecting a first set of points in the real-time ultrasound image further includes selecting these points using a peripheral device.

42. The method as defined in claim 34 wherein the correlated two-dimensional image is generated from correlating the real-time ultrasound image with the preacquired three-dimensional image data set.

43. The method as defined in claim 42 wherein correlating includes performing at least one of registration, localization, and calibration.

44. A method for detecting organ-matter shift in a patient, the method comprising:

obtaining a preacquired image of the patient;

obtaining a real-time image of the patient;

correlating the real-time image and the preacquired image to obtain a correlated image;

selecting a first set of points on one of said images; and displaying a corresponding second set of points on another one of said images, wherein said corresponding second set of points represents the organ-matter shift in the patient.

45. The method as defined in claim 44 wherein determining a preacquired image of the patient includes obtaining a three-dimensional image data set of the patient.

46. The method as defined in claim 45 wherein obtaining a real-time image of the patient includes obtaining a real-time ultrasound image of the patient.

47. The method as defined in claim 46 wherein selecting a first set of points includes selecting a first set of points on the real-time ultrasound image.

48. The method as defined in claim 47 wherein displaying a corresponding second set of points includes displaying a corresponding second set of points on the correlated two-dimensional image.

49. The method as defined in claim 48 further comprising selecting the corresponding second set of points on the correlated two-dimensional image.

50. The method as defined in claim 49 further comprising determining a vector representing at least one of a distance and a direction of the organ-matter shift.

51. The method as defined in claim 50 further comprising displaying the vector representing at least one of the distance and the direction of the organ-matter shift.

* * * * *